United States Patent [19]

Mallamo et al.

[11] Patent Number: 5,498,616
[45] Date of Patent: Mar. 12, 1996

[54] CYSTEINE PROTEASE AND SERINE PROTEASE INHIBITORS

[75] Inventors: John P. Mallamo, Glenmore; Ron Bihovsky; Sankar Chatterjee, both of Wynnewood, all of Pa.; Rabindranath Tripathy, Pennsville, N.J.

[73] Assignee: Cephalon, Inc., West Chester, Pa.

[21] Appl. No.: 334,249

[22] Filed: Nov. 4, 1994

[51] Int. Cl.⁶ .................. A61K 31/41; A61K 31/415; A61K 31/44; C07D 249/04
[52] U.S. Cl. .................. 514/300; 514/242; 514/243; 514/256; 514/259; 514/303; 514/359; 514/395; 514/398; 544/182; 544/183; 544/184; 544/279; 544/287; 544/319; 546/117; 546/118; 548/255; 548/256; 548/259; 548/305.1; 548/309.7; 548/310.1; 548/311.4; 548/336.1; 548/341.1; 548/341.5; 548/342.1
[58] Field of Search .................. 544/183; 546/117; 546/118; 548/256, 259, 305.1, 309.7, 310.1, 255, 336.1, 341.1, 341.5, 342.1; 514/243, 300, 359, 395, 398

[56] References Cited

U.S. PATENT DOCUMENTS

| | | | |
|---|---|---|---|
| 5,328,916 | 7/1994 | Raddatz et al. | 514/318 |
| 5,374,623 | 12/1994 | Zimmerman et al. | 514/17 |

FOREIGN PATENT DOCUMENTS

| | | |
|---|---|---|
| 0603769A1 | 12/1993 | European Pat. Off. . |
| WO94/04172 | 3/1994 | WIPO . |

OTHER PUBLICATIONS

Carpino, L. A., "1–Hydroxy–7–azabenzotriazole. An efficient Peptide Coupling Additive", *J. Am. Chem. Soc.* 1993, 115, 4397–4398.

Deshpande et al., "Differential Distribution of Calpain in Human Lymphoid Cells", *Neurochem. Res.* 18:767–773 (1993).

Greene, T. W. et al., *Protective Groups in Organic Synthesis*, pp. 15 and 48, John Wiley & Sons, New York, 1991.

Harbeson. S. L. et al., "Inhibition of Aminopeptidases by Peptides Containing Ketomethylene and Hydroxyethylene Amide Bond Replacements", *J. Med. Chem.* 1989, 32, 1378–.

Hayashi et al., "Activation of Intracellular Calcium–Activated Neutral Proteinase in erythrocytes and its Inhibition by Exogenously Added Inhibitors", *Biochem. Biophys. Acta* 1991, 1094, 249–256.

Hoffman, R. V. et al., "A New Chiral Alkylation Methodology for the Synthesis of 2–Alkyl–4–Ketoacids in High Optical Purity Using 2–Trifyloxy Esters", *Tetrahedron Lett.* 1993, 34(13), 2051–2054.

Konig, W. et al., "Eine neue Methode zur Synthese von Peptiden: Aktivierung der Carboxylgruppe mit Dicyclohexylcarbodiimid unter Zusatz von 1–Hydroxybenyotriazolen", *Chem. Ber.* 1970, 103, 788–798.

Laemmli, U. K., "Cleavage of Structural Proteins During the Assembly of the Head of Bacteriophage T4", *Nature* 1970, 227, 680–685.

McGowan et al., "Inhibition of Calpain in Intact Platelets by the Thiol Protease Inhibitor E–64d", *Biochem. Biophys. Res. Commun.* 1989, 158, 432–435.

Mehdi et al., "Inhibition of the Proteolysis of Rat Erythrocyte Membrane Proteins by a Synthetic Inhibitor of Calpain", *Biochem. Biophys. Res. Commun.* 1988, 157, 1117–1123.

*Remington's Pharmaceutical Sciences* (Mack Pub. Co., Easton, PA, 1980).

Roberts–Lewis et al., "Immunolocalization of Calpain I–mediated Spectrin Degradation to Vulnerable Neurons in the Ischemic Gerbil Brain", *J. Neurosci.* 1994, 14, 3934–3944.

Seng, F. et al., "Eine einfache Synthese von 1–Hydroxybenzimidazol–2–carbonsaure", *Synthesis* 1975, pp. 703–704.

Towbin et al., "Electrophoretic Transfer of Proteins from Polyacrylamide Gels to Nitrocellulose Sheets: Procedure and Some Applications", *PNAS* 1979, 76, 4350–4354.

Seng, F. et al., "1,3–Dihydroxy–2–N–alkyliminobenizimidazoline", *Synthesis* 1975, pp. 703–704.

*Primary Examiner*—Richard L. Raymond
*Attorney, Agent, or Firm*—Woodcock Washburn Kurtz Mackiewicz & Norris

[57] ABSTRACT

The present invention is directed to irreversible inhibitors of serine and cysteine proteases which most preferably contain a 1-oxytriazole or 1-oxyimidazole functionality. Methods for the use of the protease inhibitors are also described.

18 Claims, No Drawings

CYSTEINE PROTEASE AND SERINE PROTEASE INHIBITORS

FIELD OF THE INVENTION

We have discovered and in this patent document we disclose novel inhibitors of cysteine or serine proteases, methods for making our novel compounds, and methods for using our novel compounds. We refer to our compounds as "heterocyclic-N-hetero atom methyl ketones."

BACKGROUND OF THE INVENTION

Numerous cysteine and serine proteases have been identified in human tissues. A "protease" is an enzyme which degrades proteins or peptides into smaller components. The terms "cysteine protease" and "serine protease" refer to proteases which are distinguished by the presence of a cysteine or serine residue which plays a critical role in the catalytic process. Mammalian systems, including humans, normally degrade and process proteins via a variety of mechanisms including the actions of cysteine and serine proteases. However, when present at elevated levels or when abnormally activated, cysteine and serine proteases are involved in pathophysiological processes.

For example, calcium-activated neutral proteases ("calpains") comprises a family of intracellular cysteine proteases which are ubiquitously expressed in mammalian tissues. Two major calpains have been identified: calpain I and calpain II. While calpain II is the predominant form in many tissues, calpain I is thought to be the predominant form in pathological conditions of nerve tissues. The calpain family of cysteine proteases has been implicated in many diseases and disorders, including neurodegeneration, stroke, Alzheimer's disease, amyotrophy, motor neuron damage, acute central nervous system injury, muscular dystrophy, bone resorption, platelet aggregation, cataracts and inflammation. Calpain I has been implicated in excitatory amino-acid induced neurotoxicity disorders including ischemia, hypoglycemia and epilepsy. The lysosomal cysteine protease cathepsin B has been implicated in the following disorders: arthritis, inflammation, myocardial infarction, tumor metastasis, and muscular dystrophy. Other lysosomal cysteine proteases include cathepsins C, H, L and S. Interleukin-1β converting enzyme ("ICE") is a cysteine protease which catalyzes the formation of interleukin-1β. Interleukin-1β is an immunoregulatory protein implicated in the following disorders and diseases: inflammation, diabetes, septic schock, rheumatoid arthritis, and Alzheimer's disease. ICE has also been linked to the apoptotic cell death of neurons which is implicated in a variety of neurodegenerative disorders including Parkinson's disease, ischemia and amyotrophic lateral sclerosis (ALS).

Cysteine proteases are also produced by various pathogens. The cysteine protease clostripain is produced by *Clostridium histolyticum*. Other proteases are produced by *Trpanosoma cruzi*, malaria parasites *Plasmodium falciparum* and *P. vinckei* and streptococcus strains. Hepatitis A viral protease(HAV 3) C is a cysteine protease essential for processing of picornavirus structural proteins and enzymes.

Exemplary serine proteases implicated in degenerative disorders include thrombin, human leukocyte elastase, pancreatic elastase, chymase and cathepsin G. Specifically, thrombin is produced in the blood coagulation cascade, cleaves fibrinogen to form fibrin and activates Factor VIII; thrombin is implicated in thrombophlebitis, thrombosis and asthma. Human leukocyte elastase is implicated in tissue degenerative disorders such as rheumatoid arthritis, osteoarthritis, atherosclerosis, bronchitis, cystic fibrosis, and emphysema. Pancreatic elastase is implicated in pancreatitis. Chymase, an enzyme important in angiotensin synthesis, is implicated in hypertension, myocardial infarction, and coronary heart disease. Cathepsin G is implicated in abnormal connective tissue degradation, particularly in the lung.

Given the link between cysteine or serine proteases and various debilitating disorders, compounds which inhibit these proteases would be useful and would provide an advance in both research and clinical settings.

SUMMARY OF THE INVENTION

We have developed novel cysteine and serine protease inhibitors which we refer to as "heterocyclic-N-hetero atom methyl ketones." They are represented by the following formula:

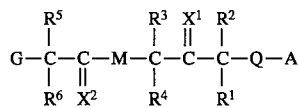

Constituent members are defined infra. Preferred embodiments are heterocyclic-N-oxy methyl ketones represented by the following formula:

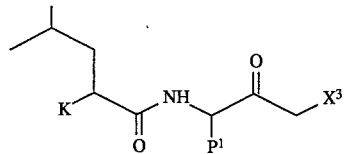

Constituent members are defined infra.

Our compounds are useful for the irreversible inhibition of cysteine and serine proteases. Beneficially, the compounds find utility in a variety of settings. For example, in a research arena, the claimed compounds can be used, for example, as standards to screen for natural and synthetic cysteine protease and serine protease inhibitors which have the same or similar functional characteristics as the disclosed compounds. In a clinical arena, our compounds can be used to alleviate, mediate, reduce and/or prevent disorders which are associated with abnormal and/or aberrant activity of cysteine proteases and/or serine proteases.

We also disclose methodologies for making our heterocyclic-N-hetero atom methyl ketones.

These and other features of our compounds will be set forth in expanded form as our disclosure continues.

DETAILED DESCRIPTION OF THE PREFERRED EMBODIMENTS

We have discovered novel cysteine and serine protease inhibitors which are represented by the general formula:

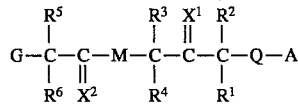

wherein:

M is O, $NR^7$ or $CR^1R^2$, and most preferably $NR^7$;

$X^1$ is O, S or $NR^7$, and preferably O;

$X^2$ is O, S, $NR^7$ or two hydrogen atoms, and preferably O;

Q is O, S or NR$^1$, and preferably O;

R$^1$ and R$^2$ are independently H, alkyl having from 1 to 10 carbons, heteroaryl having from 1 to 10 carbons, alkanoyl having from 1 to 10 carbons, or aroyl, wherein the alkyl, heteroaryl, alkanoyl and aroyl groups are optionally substituted with J;

R$^3$, R$^4$, R$^5$ and R$^6$ are independently H, alkyl having from 1 to 10 carbons, aryl, or heteroaryl, wherein the alkyl, aryl and heteroaryl groups are optionally substituted with J;

Preferably, R$^1$, R$^2$ and R$^4$ are H; and R$^3$ is H, n-butyl, isobutyl or benzyl;

R$^7$ and R$^8$ are independently H, alkyl having from 1 to 10 carbons, aryl, or heteroaryl, wherein the alkyl, aryl and heteroaryl groups are optionally substituted with J;

J is halogen, COOR$^7$, R$^7$OCO, R$^7$OCONH, OH, CN, NO$_2$, NR$^7$R$^8$, N=C(R$^7$)R$^8$, N=C(NR$^7$R$^8$)$_2$, SR$^7$, OR$^7$, phenyl, naphthyl, heteroaryl, or a cycloalkyl group having from 3 to 8 carbons;

G is NH$_2$, NHR$^1$, CH$_2$R$^1$, CH$_2$C(O)B, carbobenzyloxy-NH, succinyl-NH, R$^7$O-succinyl-NH, R$^7$OC(O)NH, —CH$_2$C(O)-(xanthen-9-yl), CH$_2$COR$^9$ where R$^9$ is an alkyl, aryl, or arylalkyl group of up to 13 carbons; or AA$^1$NHC(O)OCH$_2$C$_6$H$_5$ where AA$^1$ is one of the 20 natural amino acids or its opposite antipode;

B is alkyl having from 1 to 10 carbons, aralkyl having from 1 to 10 carbons, aryl having 1 to 3 carbocyclic rings, or heteroaryl having 1 to 3 rings, wherein the alkyl, aralkyl, aryl and heteroaryl groups are optionally substituted with J; and A has the structure:

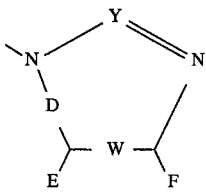

wherein:
Y is N or CR$^1$;
W is a double bond or a single bond;
D is C=O or a single bond;
E and F are independently R$^1$, R$^2$, J, or when taken together E and F comprise an aliphatic carbocyclic ring having from 5 to 7 carbons, an aromatic carbocyclic ring having from 5 to 7 carbons, an aliphatic heterocyclic ring having from 5 to 7 atoms, or an aromatic heterocyclic ring having from 5 to 7 atoms; wherein:
the aliphatic heterocyclic ring and the aromatic heterocyclic ring each have from 1 to 4 heteroatoms; and the aliphatic carbocyclic ring, the aromatic carbocyclic ring, the aliphatic heterocyclic ring, and the aromatic heterocyclic ring are each optionally substituted with J.

Preferred embodiments of the invention have the formula:

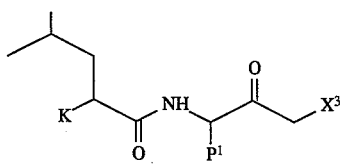

wherein:
K is NHC(O)OCH$_2$C$_6$H$_5$, —CH$_2$C(O)-(xanthen-9-yl) or —CH$_2$C(O)CH(C$_6$H$_5$)C$_2$H$_5$.
p$^1$ is isobutyl, isopropyl, benzyl, ethyl or carboxyalkyl of 2-9 carbons; and
X$^3$ has the formula:

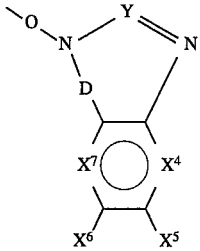

wherein:
D is C=O or a single bond;
X$^4$ is CH, CCl, CCH$_3$, CF or N;
X$^5$ is H, CH$_3$, Cl, OCH$_3$ or F;
X$^6$ is H, CH$_3$, Cl, F, OCH$_3$, CF$_3$, ethyl or phenyl;
X$^7$ is N, CCl, CH, COCH$_3$ or CF; and
Y is N or CH.

In some preferred embodiments, K is —CH$_2$C(O)-(xanthen-9-yl) or carbobenzyloxy-NH, and in other preferred embodiments, p$^1$ is benzyl, isobutyl or ethyl.

In further preferred embodiments Y is N. Preferably, X$^3$ is O-1-oxybenzotriazole, or X$^7$ is N, or Y is CH, or Y is N and D is C=O.

In some embodiments Q is NR$^1$, or R$^3$ and R$^4$ are both not H. In other embodiments one of R$^1$ or R$^2$ is a group other than H. In further embodiments, X$^1$ is S or NR$^7$, or M is O or CR$^1$R$^2$.

In other embodiments X$^2$ is S, NR$^1$, or two hydrogen atoms, or K has the formula:

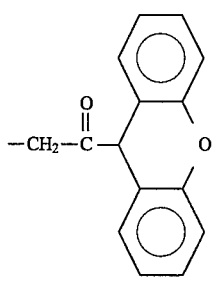

As used herein, the term "alkyl" is meant to include straight-chain, branched and cyclic hydrocarbon groups such as, for example, ethyl, isopropyl and cyclopropyl groups. Preferred alkyl groups have 1 to about 10 carbon atoms. "Cycloalkyl" groups are cyclic alkyl groups. "Aryl" groups are aromatic cyclic compounds including but not limited to phenyl, tolyl, benzyl, naphthyl, anthracyl, phenanthryl, pyrenyl, and xylyl. The term "carbocyclic," as used herein, refers to cyclic groups in which the ring portion is composed solely of carbon atoms. The term "heterocyclic" refers to cyclic groups in which the ring portion includes at least one heteroatom such as O, N or S. "Heteroalkyl" groups are heterocycles containing solely single bonds within their ring portions, i.e. saturated heteroatomic ring systems. "Alkanoyl" groups are those which contain an alkyl portion linked through a carbonyl group. "Aroyl"

groups are those which contain an aryl portion linked through a carbonyl group. "Aralkyl" groups have both aryl and alkyl portions, and are attached through their alkyl portions.

Because the disclosed compounds are useful in inhibiting the activity of serine and cysteine proteases, and because the usefulness of such compounds can be applied to both research and therapeutic settings, methodologies for inhibiting the activity of cysteine and serine proteases by contacting the protease with a compound of the invention include providing the compound to a mammal, including a human, as a medicament or pharmaceutical agent.

As used herein, the term "contacting" means directly or indirectly causing at least two moieties to come into physical association with each other. Contacting thus includes physical acts such as placing the moieties together in a container, or administering moieties to a patient. Thus, for example, administering a compound of the invention to a human patient evidencing a disease or disorder associated with abnormal and/or aberrant activity of such proteases in a method for inhibiting the enzymatic activity of such protease which are associated with disease or disorder, falls within the scope of the definition of the term "contacting."

As used herein, the terms "inhibit" and "inhibition" mean having an adverse effect on enzymatic activity. The term "irreversible," when used to modify "inhibit" and "inhibition," means that such adverse effect on catalytic activity can not be reversed once it is initiated. Inhibition of cysteine or serine protease activity can be determined using a variety of methodologies. Two convenient methodologies are preferred. The first involves determining the rate of inactivation of a protease using a compound of the invention; the second involves determining the percent inhibition of a defined amount of the protease by a compound of the invention. With respect to the cysteine protease calpain I, a whole cell assay, which measures inhibition of calpain I activity via a decrease in the amount of cleavage of a preferred calpain I substrate, α-spectrin, is also useful in determining the inhibition of catalytic activity.

In a research environment, preferred compounds having defined attributes can be used to screen for natural and synthetic compounds which evidence similar characteristics of inhibiting protease activity. The compounds can also be used in the refinement of in vitro and in vivo models for determining the effects of inhibition of particular proteases on particular cell types or biological conditions.

Pharmaceutically acceptable salts of the cysteine and serine protease inhibitors also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable ammonium salts are ammonium salt and tetramethylammonium salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients and carriers. The compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, trans-dermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in Remington's Pharmaceutical Sciences (Mack Pub. Co., Easton, Pa., 1980). Formulations for parenteral administration may contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials of this invention can be employed as the sole active agent in a pharmaceutical or can be used in combination with other active ingredients.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 µg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the invention are mechanism-based irreversible inhibitors of cysteine and serine proteases which we believe, although not wishing to be bound thereby, provide a novel mechanism of protease inactivation. The inhibitors most preferably contain a 1-oxytriazole, 3-oxytriazin-4-one, or 1-oxyimidazole functionality. It has been found that the compounds of the invention are irreversible inhibitors. While not wishing to be bound by any specific theory, it is believed that linkage through the N-hetero, preferably N-oxy bond, makes the 1-oxytriazole, 3-oxytriazin-4-one, or 1-oxyimidazole moiety a superior leaving group, thus facilitating inactivation upon interaction with the target protease. Scheme 1 depicts a proposed mechanism of inactivation of a cysteine protease by an inhibitor of the invention:

calpain, nitrocellulose sheets were first blocked in 5% Blotto (5% Carnation instant milk/10 mM Tris/150 mM NaCl) for 30 minutes, followed by incubation for 1 hour in antibody directed against Calpain I (rabbit anti-human calpain I polyclonal sera, 1:1000 dilution in 5% Blotto). After three 5 minutes washes in 10 mM Tris/150 mM NaCl/.05% Tween 20 the nitrocellulose was incubated for 1 hour in secondary alkaline phosphatase conjugated antibody (Biorad Cat#170-6518 1:2000 in 5% Blotto). After three 5 minutes washes in 10 mM Tris/150 mM NaCl/.05% Tween 20 and 1 wash in 10

Scheme 1

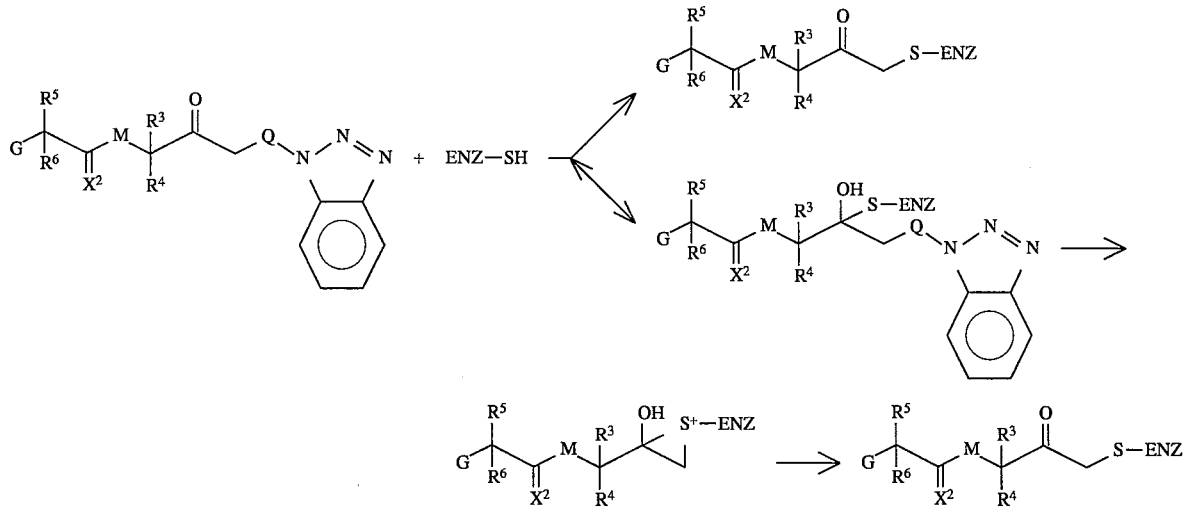

The invention is further illustrated by way of the following examples which are intended to ellucidate the invention. These examples are not intended, nor are they to be construed, as limiting the scope of the disclosure nor the appended claims.

EXAMPLE 1A

Inhibition and Rate of Cysteine Protease Activity

To evaluate inhibitory activity of our compounds, stocks (40 times concentrated) of each compound to be tested were prepared in 100% anhydrous dimethyl sulfoxide (DMSO) and 5 µl of each inhibitor preparation was aliquoted into each of three wells of a 96 well plate. Calpain I was purified from human red blood cells using a modification of the method described by Lee, W. J. et al. (Biochem. Internatl. (1990)22(1): 163–171). Briefly, 3 units of packed outdated red blood cells were washed 3x by repeated centrifugation at 500 rpm for 10 minutes through 900 mls of 0.9% NaCl. Cells were lysed in 20 mM Tris/1 mM EDTA/1 mM EGTA/5 mM mercaptoethanol (Buffer A) and centrifuged for 1 hour at 12,000 rpm in a GSA rotor using a Sorval centrifuge. The supernatant was collected and applied to a DEAE-sepharose FF column equilibrated in Buffer A +25 mM NaCl. After washing the column in Buffer A+25 mM NaCl, the bound protein was eluted at 117 ml/hr with a 25 mM to 150 mM NaCl linear gradient in Buffer A collecting 200, 10 ml fractions. Two µl of every fifth fraction was applied to nitrocelluose using a dot blot apparatus and calpain containing fractions identified by Western analysis. For detection of mM Tris/150 mM NaCl the nitrocellulose was incubated for up to 2 hours in a colorimetric substrate solution (Biorad Alakaline Phosphatase Substrate conjugate kit, cat#170-6432). The reaction was stopped by washing in water. After fractions containing calpain, and those in between, were pooled, solid ammonium sulfate was added to achieve a 30% solution and the mixture stirred for 1 hour at 4° C. Following collection of the precipitate by centrifugation for 1 hour at 4° C. at 12K rpm in a GSA rotor, the supernatant was collected and brought to 45% in ammonium sulfate. After stirring for 1 hour at 4° C., centrifugation was repeated. The supernatant was discarded and the precipate resuspended in approximately 7 mls and dialyzed overnight at 4° C. against Buffer A+50 mM NaCl. The sample was then applied to a S300 gel filtration column preequilibrated in Buffer A+50 mM NaCl, washed and eluted at a flow rate of 20 ml/hr, collecting 200, 4 ml fractions. The peak of calpain was determined by assaying aliquots of every fifth fraction for enzyme activity monitored by the hydrolysis of a fluorogenic dipeptide substrate as described below. The peak fractions were pooled and the enzyme preparation used to test compounds for inhibitory activity. As an alternate to enzyme isolated from tissue sources, recombinant human calpain I has also been used to monitor compounds for inhibitory activity.

The foregoing enzyme preparation was diluted into assay buffer (i.e., 50 mM Tris, 50 mM NaCl, 1 mM EDTA, 1 mM EGTA, and 5 mM β-mercaptoethanol, pH 7.5 including 0.2 mM Succ-Leu-Tyr-MNA) and 175 µl aliquoted into the same wells containing the independent inhibitor stocks as well as to positive control wells containing 5 µl DMSO, but no compound. To start the reaction, 20 µl of 50 mM CaCl₂ in assay buffer was added to all wells of the plate, excepting three, which were used as background signal baseline controls. Substrate hydrolysis was monitored every 5 minutes for a total of 30 minutes using Flouroskan II (ex=340 mM; em=430 mM). Substrate hydrolysis in the absence of inhibitor was linear for up to 15 minutes.

To demonstrate activity against two other cysteine proteases, cathepsin B (Calbiochem, cat#219364) and cathepsin L (Calbiochem, cat#219402), assays were performed substantially the same as outlined above except that the cathepsin B and cathepsin L were diluted into a different assay buffer consisting of 50 mM sodium acetate (pH 6.0)/1 mM EDTA/1 mM ditheothreitol and 2 the substrate used was Cbz-Phe-Arg-AMC (Bachem cat#I-1160; 0.1 mM for cathepsin B; .006 mM for cathepsin L). Additionally, the order of reagents added to the plate was altered because both enzymes are constitutively active. Following inhibitor addition to the plates appropriate 2× concentrated stock dilutions of the enzyme preparations were made in assay buffer and 100 ul added to each well. The assay was initiated by addition of 100 ul of 2× concentrated stock dilution of substrate in assay buffer. Substrate hydrolysis was monitored using a Fluoroskan II (ex=390 nm; em=460 mM).

Inhibition of enzyme activity was calculated as the percent decrease in the rate of substrate hydrolysis in the presence of inhibitor ($v_i$) relative to the rate in its absence ($v_o$). Comparison between $v_o$ and $v_i$ was made within the linear range for substrate hydrolysis. For screening, compounds were tested at 10 µM. Compounds having ≧50% inhibition at 10 µM were considered active. Apparent second order rate constants were determined from analysis of reaction progress curves under pseudo-first order conditions. Each determination represents the mean of three or more independent single cuvette analyses continually monitored via a Perkin-Elmer LS50B spectrofluorimeter. The rate of inhibition of hydrolysis was obtained by fitting the curve to the exponential equation (1):

$$y = Ae^{-k_{obs} \cdot t} + B \qquad (1)$$

where y ($P_t$) is the product formed at time t. A and B are constants. A, the amplitude of the reaction, is given by $[P_o - P_\infty]$ and B ($= P_\infty$) is the maximal product formed when the reaction is determined as $k_{obs}/[I]$. This was corrected for the presence of equation (2):

$$k_2 = k_{app}(1 + [S]/K_m) \qquad (2)$$

Values for $k_2$ are provided in Table IA.

TABLE IA

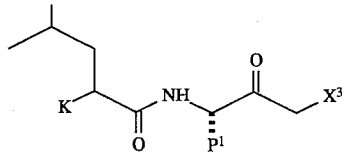

K = ZNH, L or W

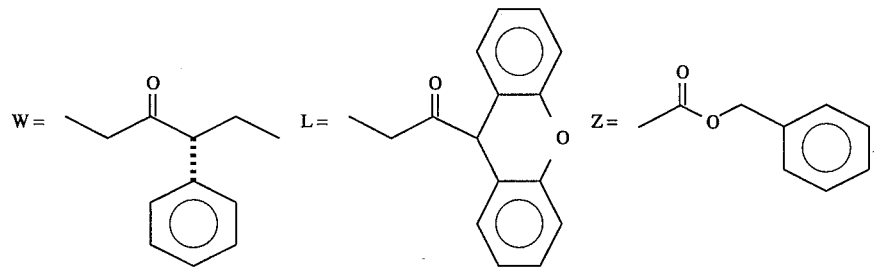

| Compound of Example: | X₃ | P₁ | K | $k_2 \times 10^3$ (M⁻¹ s⁻¹) A* | B* | C* |
|---|---|---|---|---|---|---|
| 3 | 1-oxybenzotriazole | Benzyl | ZNH | 150 | 100 | 117 |
| 4 | 1-oxybenzotriazole | i-Butyl | ZNH | 175 | | 19 |
| 5 | 1-oxybenzotriazole | Ethyl | ZNH | 63 | 3000 | 443 |
| 6 | 3-oxy-(3H)-triazolo[4,5-b]pyridine | Benzyl | ZNH | 184 | 40 | 107 |
| 7 | 6-trifluoromethyl-1-oxybenzotriazole | Benzyl | ZNH | 160 | | 18 |
| 8 | 6-chloro-1-oxybenzotriazole | Benzyl | ZNH | 101 | | |
| 9 | 6-methoxy-1-oxybenzotriazole | Benzyl | ZNH | 125 | | 52 |
| 10 | 6-fluoro-1-oxybenzotriazole | Benzyl | ZNH | 50 | | |
| 11 | 6-chloro-5-methyl-1-oxybenzotriazole | Benzyl | ZNH | 98 | | 28 |
| 12 | 4-methyl-1-oxybenzotriazole | Benzyl | ZNH | 46 | | |
| 13 | 5-chloro-6-methyl-1-oxybenzotriazole | Benzyl | ZNH | 116 | | 29 |
| 14 | 4-chloro-1-oxybenzotriazole | Benzyl | ZNH | 157 | | |
| 15 | 6-phenyl-1-oxybenzotriazole | Benzyl | ZNH | 77 | | 16 |
| 16 | 4,5,6,7-tetrafluoro-1-oxybenzotriazole | Benzyl | ZNH | 93 | | |
| 17 | 5-chloro-1-oxybenzotriazole | Benzyl | ZNH | 164 | | |
| 18 | 5,6-dichloro-1-oxybenzotriazole | Benzyl | ZNH | 65 | | 115 |

TABLE IA-continued

[Structure: K-C(=O)-NH-CH(P¹)-C(=O)-CH₂-X³]

K = ZNH, L or W

[Structures shown for W, L, and Z]

| Compound of Example: | X₃ | P₁ | K | $k_2 \times 10^3$ $(M^{-1} s^{-1})$ A* | B* | C* |
|---|---|---|---|---|---|---|
| 19 | 1-oxy-(1H)-triazolo[4,5-b]pyridine | Benzyl | ZNH | 57 | | |
| 20 | 4,5,6,7-tetrachloro-1-oxybenzotriazole | Benzyl | ZNH | 1.3 | | |
| 21 | 4,6,7-trichloro-1-oxybenzotriazole | Benzyl | ZNH | 1.8 | | 10 |
| 22 | 1-oxybenzimidazole | Benzyl | ZNH | 4 | | |
| 23 | 4,5-dichloro-1-oxybenzotriazole | Benzyl | ZNH | 64 | | |
| 24 | 5-chloro-6-ethyl-1-oxybenzotriazole | Benzyl | ZNH | 84 | | 30 |
| 25 | 4,5-difluoro-1-oxybenzotriazole | Benzyl | ZNH | 67 | | 300 |
| 26 | 6-methyl-1-oxybenzotriazole | Benzyl | ZNH | 112 | | |
| 27 | 5-methyl-1-oxybenzotriazole | Benzyl | ZNH | 230 | | |
| 28 | 3-oxybenzotriazin-4-one | Benzyl | ZNH | 122 | 70 | 7 |
| 29 | 6,7-dimethoxy-3-oxybenzotriazin-4-one | Benzyl | ZNH | 171 | | |
| 30 | 6-chloro-3-oxybenzotriazin-4-one | Benzyl | ZNH | 180 | | |
| 31 ** | 3-oxybenzotriazin-4-one | i-Butyl | ZNH | 46 | | |
| 39 | 1-oxybenzotriazole | Benzyl | L | 46 | | 55 |
| 40 ** | 1-oxybenzotriazole | i-Butyl | L | 2.7 | | 48 |
| 46 | 1-oxybenzotriazole | Benzyl | W | 3 | | |

*A = Calpain I; B = Cathepsin L; C = Cathepsin B
**Examples 32–38 and 41–45 are synthetic intermediates in the preparation of the compounds of examples 39–40 and 46, respectively.

EXAMPLE 1B

Inhibition of Serine Protease Activity

To demonstrate activity against the serine protease α-chymotrypsin (Sigma Chem. Co. cat#C-3142) the protocol of Example 1A was followed except that the enzyme was diluted into assay buffer consisting of 50 mM Hepes (pH 7.5)/0.5M NaCL and the final substrate concentration used was 0.03 mM Succ-Ala-Ala-Pro-Phe-AMC (Bachem, Inc. Cat#1-1465). Additionally, because α-chymotrypsin is not a calcium sensitive enzyme and is constituitively active, following addition of inhibitor stocks to the 96 well plates, 100 ul of a 2 fold concentrated stock of enzyme in dilution buffer was first added and the reaction started by addition of 100 ul of a 2 fold concentrated stock of substrate in assay buffer. Substrate hydrolysis was monitored every 5 minutes up to 30 minutes using a Fluoroskan II (em=390 mM ex=460 mM). Results, expressed as % inhibition of α-chymotrypsin at 10 μM, are presented in Table IB.

TABLE IB

| Compound of Example: | % Inhibition of α-Chymotrypsin at 10 μM |
|---|---|
| 3 | 86 |
| 5 | 34 |
| 6 | 81 |
| 7 | 99 |
| 9 | 83 |
| 10 | 89 |
| 11 | 100 |
| 12 | 94 |
| 22 | 91 |
| 28 | 82 |
| 39 | 100 |
| 40 | 100 |

EXAMPLE 1C

Inhibition of Calpain Activation in Intact Cells

Sodium Dodecy/Sulfate-Polyacrylamide Gel Electrophoresis (SDS/PAGE)/Coomassie stain/Densitometric analysis of calpain cleavage of endogenous substrates has served as a standard method for measuring inhibition of calpain activation in intact cell systems following exposure to calcium and ionophore (Mehdi et al., 1988, *Biochem. Biophys. Res. Commun.*, 157:1117–1123; McGowan et al., 1989, *Biochem. Biophys. Res. Commun.* 158:432–435; Hayashi et al., 1991, *Biochem. Biophys. Acta.* 1094:249–256). In our analysis, we monitored the degradation of a preferred calpain substrate, the α-subunit of non-erythrocyte spectrin, using two independent antibodies which recognize the two 150 kDa cleavage products specifically generated by calpain proteolysis (Roberts-Lewis et al., 1994, *J. Neurosci.* 14:3934–3944). The use of these antibodies has greatly facilitated the evaluation of calpain inhibition in intact cell systems. For intact cell assays, the human lymphoid cell line Molt-4, in which the calpain I isozyme predominates (Deshpande et al., 1993, *Neurochem. Res.* 18: 767–773) was chosen for inhibitor screening. The effectiveness of our compounds in intact Molt-4 cells is measured as a decrease in the amount of calpain-generated spectrin breakdown products compared to the amount generated in the presence of calcium and ionophore alone. Molt-4 cells were first washed and subsequently resuspended in Hepes-Buffered Saline (5.4 mM KCl, 120 mM NaCl, 25 mM glucose, 1.5 mM $MgSO_4$, 1 mM sodium pyruvate, 20 mM Hepes pH 7.0) to $1 \times 10^7$ cells/ml. Test compounds were first solubilized in DMSO to 50 mM and subsequently diluted into Hepes-Buffered saline to a final concentration of 200 µM maintaining 8% DMSO final concentration. Five microliters of inhibitor stock solutions (200 µM) were then aliquoted into each of three wells of a 96 well microtiter plate, followed by 100 µl of cell suspension. Routinely, cells were preincubated with 40 µM inhibitor for 10 minutes. Subsequently, 100 µl of Hepes-buffered saline solution containing 20 µM calcium ionophore (ionomycin (Sigma, St. Louis, Mo., I-0634)) and 5 mM $CaCl_2$ was added to the cells and allowed to incubate for up to 30 minutes. The calcium was then chelated by addition of 2 µl of 1M EDTA and the cells were harvested by centrifugation in a Beckman table top centrifuge. The supernatant was removed and the cells lysed by addition of 20 mM Tris-HCl pH 8.0/1% NP-40/.137M NaCl/13 mM EDTA/10 µg/ml aprotinin/10 µg/ml leupeptin/.1M PMSF. Insoluble material is removed by centrifugation and the protein concentration of the lysates determined by a BCA micro protein assay (Pierce, Inc., Rockford, Ill.). Twenty micrograms of each sample was then applied to a 6% SDS-PAGE gel and electrophoresed for 45 min at 200 V (Laemmeli, U.K. 227 *Nature* 680, 1970). Electrophoresed protein is then transferred to nitrocellulose (Towbin, H et al. 76 *PNAS* 4350, 1979). For detection of spectrin breakdown products, nitrocellulose sheets were first blocked in 5% Blotto (5% Carnation instant milk/10 mM Tris/150 mM NaCl, pH 8.0) for 30 minutes, followed by incubation for 1 hour in antibody directed against spectrin breakdown products (Ab 38 and/or 41; Roberts Lewis et al., *J. Neurosci* 14, 3934–3944, 1994, 1:500 dilution in 5% Blotto). After three 5 minute washes in 10 mM Tris/150 mM NaCl/.05% Tween 20 the nitrocellulose is incubated for 1 hour in secondary alkaline phosphatase conjugated antibody (Biorad, Hercules CA Cat#170-6518 1:2000 in 5% Blotto). After three 5 minutes washes in 10 mM Tris/150 mM NaCl/.05% Tween 20 and 1 wash in 10 mM Tris/150 mM NaCl the nitrocellulose is incubated for up to 2 hours in a colorimetric substrate solution (Biorad Alakaline Phosphatase Substrate conjugate kit cat#170-6432). The reaction is stopped by washing in water. After the nitrocellulose sheets are dried the amount of spectrin breakdown products detected is quantified using a BioQuant-Osk image analysis system (R&M Biometrics, Inc., Nashville, Tenn.). The amount of breakdown products in compound treated cells is compared relative to the amount in non-compound treated cells and expressed as the % inhibition of breakdown products ("BDPs"). Results are presented in Table IC.

TABLE IC

| Compound of Example: | % Inhibition of BDPs (10 µM) |
|---|---|
| 3 | 67 |
| 4 | 57 |
| 5 | 56 |
| 6 | 63 |
| 8 | 57 |
| 16 | 64 |
| 19 | 54 |
| 22 | 61 |
| 25 | 52 |
| 28 | 68 |

Synthesis of Exemplary Compounds

HPLC analysis and purification of final products and intermediates was conducted under the conditions described in each example using a VyDac reverse-phase C-18 10 micron column (1.0×25 cm) at a flow rate of 3.5 ml/min. coupled to a UV detector.

The use of $Ag_2O$ in the alkylation of alcohols is described in T. W. Greene et al., *Protective Groups in Organic Synthesis*, New York, N.Y. John Wiley & Sons, Dec. 1991, pp. 15 and 48.

Starting Materials:

1-Hydroxybenzotriazole can be purchased from various commercial sources (e.g., Aldrich Chemical Company) and was used as received. All other benzotriazoles were prepared according to the procedures described in Brady, O. L. et al., *J. Chem. Soc.* 37, 2258–2267 (1960); König, W. et al., *Chem. Bet.* 103, 788–798 (1970); and Carpino, L. A., *J. Am. Chem. Soc.* 115, 4397–4398 (1993). 1-Hydroxybenzimidazole was prepared according to Seng, F. et al., *Synthesis* 1975, page 703. Leucine chloromethylketone and phenylalanine chloromethylketone can be purchased from various commercial sources (e.g., BACHEM Bioscience, Inc.) and were used as received. Amino acid or N-terminal protected dipeptide bromomethyl ketones were prepared from the corresponding diazomethylketones by treatment with HBr/AcOH or HBr (gas) according to the standard procedures cited and described in Harbeson, S. L. et al., *J. Med. Chem.* 32, 1378–1392 (1989).

EXAMPLE 2

Methods A and B are general methods for preparing compounds of the invention from halomethylketones 1 and 2.

Dipeptide halomethylketone 1; m.p. 135.5°–136.5° C.

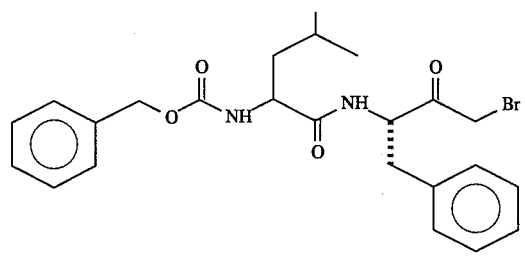

and dipeptide halomethylketone 2; m.p. 103°–104° C.

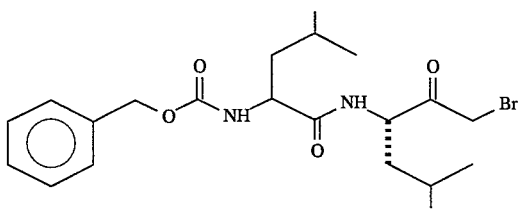

Method A: To a solution of the appropriate bromo or iodoketone (0.05–0.1 mmol) and an N-hydroxyheterocycle (1.1 eq.) in 1 mL of dimethylformamide was added Ag$_2$O (1.1–2.2 eq.) under inert atmosphere. The reaction mixture was stirred at room temperature minimizing exposure to light for 0.5–72 h. The mixture was then diluted with ethyl acetate and filtered through a pad of diatomaceous earth. The filter pad was thoroughly washed with ethyl acetate and the combined filtrates were washed twice with 1 volume of H$_2$O and 1 volume of brine. After drying over anhydrous magnesium sulfate, and filtration, the solvent was removed under reduced pressure. The desired product was isolated and purified by HPLC as described for each example.

Method B: To a solution of the appropriate bromoketone (0.1–0.15 mmol) in dry dimethylformamide was added anhydrous potassium fluoride (3.5 eq.), and the mixture was stirred at room temperature for approximately 5 min under an inert atmosphere. An N-hydroxyheterocycle (1.2 eq.) was added, and the resulting mixture was stirred for 24 h. The reaction mixture was diluted with ethyl acetate, washed successively with 1 volume each of water, saturated aqueous NaHCO$_3$, 10% aqueous citric acid, water and finally with brine. After drying over magnesium sulfate, and filtration, the solvent was removed under reduced pressure. The desired product was isolated and purified by flash chromatography and/or HPLC.

EXAMPLE 3

1-[N-[N-Benzyloxycarbonyl-L-leucyl]-3S-4-phenyl-3-amino-2-oxobutyloxy]benzotriazole.

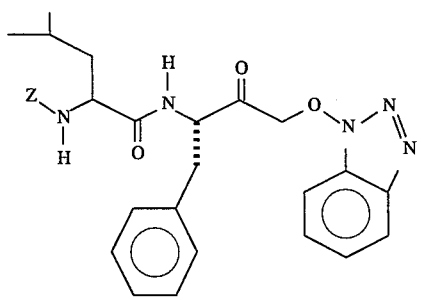

Method A; reaction time 19 h; purification: flash chromatography (hexane:ethyl acetate 1:1) followed by HPLC (reverse phase, acetonitrile :water (containing 0.1% trifluoroacetic acid) 10%–100% over 40 min) R$_t$ 30.10 min; yield 66%; mp 128.5–130 C; $^1$H NMR (300 MHz, CDCl$_3$): δ8.00 (d, 1H), 7.83 (d, 1H), 7.56 (t, 1H), 7.43 (t, 1H), 7.38–6.98 (m, 10H), 6.57 (m, 1H), 5.29 (bd, 1H), 5.06–4.9 (s overlapping with m, 4H), 4.76 (q, 1H), 4.12 (m, 1H), 3.00 (m, 2H), 1.7–1.3 (series of m, 3H), 0.98 (m, 6H); FABMS m/z 544 (MH$^+$); Anal. C (66.23), H (6.07), N (12.83); calc. C (66.29), H (6.07), N (12.89).

EXAMPLE 4

1-[N-[N-Benzyloxycarbonyl-L-leucyl]-3S-5-methyl-3-amino-2-oxohexyloxy]benzotriazole.

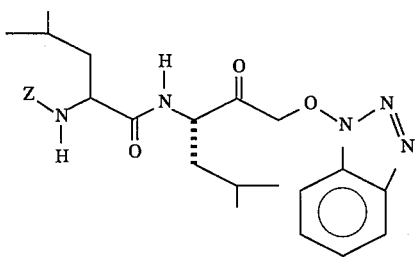

Method B; reaction time 24 h; purification: flash chromatography (hexane:ethyl acetate 1:1) followed by HPLC (reverse phase, acetonitrile:water (containing 0.1% trifluoroacetic acid) 10%–100% over 40 min) R$_t$ 29.31 min; yield 43%; $^1$H NMR (300 MHz, CDCl$_3$):δ7.96 (m, 1H), 7.81 (bd, 1H), 7.53, m, 1H), 7.44–7.16 (m, 6H), 6.7 (bd, 1H), 5.41 (m, 2H), 5.24–5.00 (s overlapping with m, 3H), 4.62 (m, 1H), 4.18 (m, 1H), 1.72–1.35 (m, 6H), 0.92 (m, 12H); FABMS m/z ( 510, MH$^+$) .

EXAMPLE 5

1-[N-[N-Benzyloxycarbonyl-L-leucyl]-3S-3-amino-2-oxopentyloxy]benzotriazole.

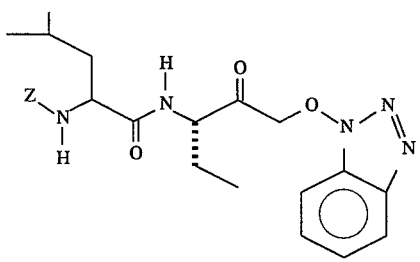

Method A; reaction time 19 h; purification flash chromatograpy (hexane:ethyl acetate 1:1) followed by HPLC (reverse phase, acetonitrile:water (containing 0.1% trifluoroacetic acid) 10%–100% over 40 min) R$_t$ 30.10 min; yield 24%; $^1$H NMR (300 MHz, CDCl$_3$): δ7.98 (d, 1H), 7.83 (bd, 1H), 7.53 (m, 1H), 7.38 (m, 1H), 7.30 (s, 5H), 6.69 (bd, 1H), 5.40 (s, 2H), 5.15 (d, 1H), 5.07 (s, 2H), 4.58 (m, 1H), 4.15 (m, 1H), 1.90 (m, 1H), 1.75–1.4 (m, 4H), 0.92 (m, 6H), 0.83 (bt, 3H); FABMS m/z (482, MH$^+$).

EXAMPLE 6

3-[N-[N-Benzyloxycarbonyl-L-leucyl]-3S-4-phenyl-3-amino-2-oxobutyloxy]-3H-triazolo[4,5-b]pyridine.

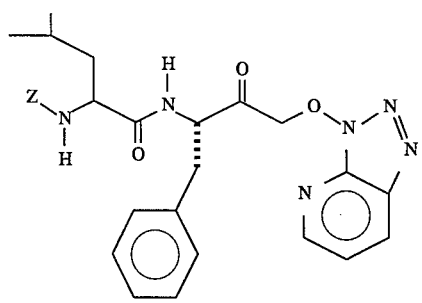

Method A; reaction time: 18 h; yield 36%; purification: HPLC (reverse phase, acetonitrile :water (containing 0.1% trifluoroacetic acid) 10%–100% over 40 min) $R_t$: 28.25 min; $^1$H NMR (300 MHz, CDCl$_3$): δ8.78 (m, 1H), 8.44 (bd, 1H), 7.49 (m, 1H), 7.44–7.12 (m, 10H), 6.83 (m, 1H), 5.43–5.00 (m, 6H), 4.16 (m, 1H), 3.35–3.05 (m, 2H), 1.69–1.35 (m, 3H), 0.92 (m, 6H); FABMS m/z (545, MH$^+$)

EXAMPLE 7

1-[N-[N-Benzyloxycarbonyl-L-leucyl]-3S-4-phenyl-3-amino-2-oxobutyloxy]-6'-trifluoromethylbenzotriazole.

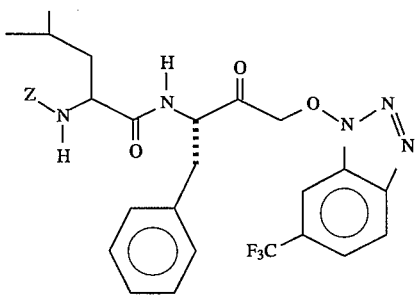

Method A; reaction time: 15 h; yield 12%; purification: HPLC (reverse phase, acetonitrile:water (containing 0.1% trifluoroacetic acid) 10%–100% over 40 min) $R_t$: 32.90 min; $^1$H NMR (300 MHz, CDCl$_3$): δ8.23 (s, 1H), 8.10 (d, 1H), 7.63 (d, 1H), 7.43–6.86 (m, 10H), 6.52 (m, 1H), 5.33 (m, 1H), 5.15–4.86 (s overlapping with m, 4H), 4.69 (m, 1H), 4.09 (m, 1H), 2.95 (m, 2H), 1.66–1.26 (m, 3H), 0.89 (m, 6H); FABMS m/z (612, MH$^+$).

EXAMPLE 8

1-[N-[N-Benzyloxycarbonyl-L-leucyl]-3S-4-phenyl-3-amino-2-oxobutyloxy]-6'-chlorobenzotriazole.

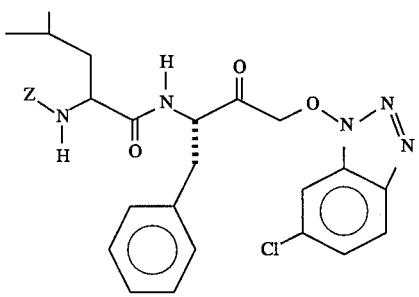

Method A; reaction time: 15 h; yield 30%; purification: HPLC (reverse phase, acetonitrile:water (containing 0.1% trifluoroacetic acid) 10%–100% over 40 min) $R_t$: 32.21 min; $^1$H NMR (300 MHz, CDCl$_3$): δ7.90 (m, 2H), 7.46–6.95 (m, 11H), 6.60 (m, 1H), 5.29 (m, 1H), 5.18–4.89 (m, 4H), 4.72 (m, 1H), 4.09 (m, 1H), 2.97 (m, 2H), *** M$^+$) Delete to M+) 1.67–1.3 (m, 3H), 0.89 (m, 6H); FABMS m/z (578, MH+).

EXAMPLE 9

1-[N-[N-Benzyloxycarbonyl-L-leucyl]-3S-4-phenyl-3-amino-2-oxobutyloxy]-6'-methoxybenzotriazole.

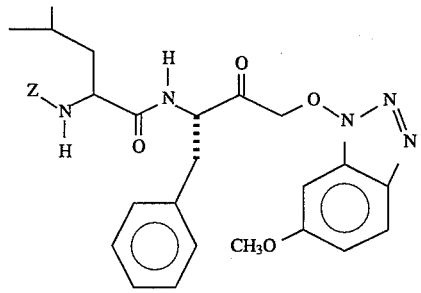

Method A; reaction time: 49 h; yield 7.5%; purification: HPLC (reverse phase, acetonitrile :water (containing 0.1% trifluoroacetic acid) 10%–100% over 40 min) $R_t$: 31.55 min; $^1$H NMR (300 MHz, CDCl$_3$): δ7.82 (dd, 1H), 7.46–6.85 (m, 12H), 6.60 (m, 1H), 5.29 (m, 1H), 5.15–4.9 (m, 4H), 4.80 (m, 1H), 4.12 (m, 1H), 3.93 (s, 3H), 3.03 (m, 2H), 1.67–1.32 (m, 3H), 0.86 (m, 6H); FABMS m/z (574.5, MH+).

EXAMPLE 10

1-[N-[N-Benzyloxycarbonyl-L-leucyl]-3S-4-phenyl-3-amino-2-oxobutyloxy]-6'-fluorobenzotriazole.

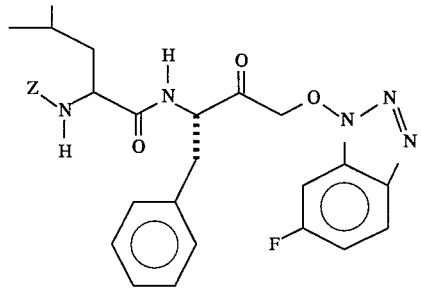

Method A; reaction time: 15 h; yield 48%; purification: HPLC (reverse phase, acetonitrile :water (containing 0.1% trifluoroacetic acid) 10%–100% over 40 min) $R_t$: 31.33 min; $^1$H NMR (300 MHz, CDCl$_3$): δ7.98 (m, 2H), 7.52 (bd, 1H), 7.43–7.09 (m, 10H), 6.69 (m, 1H), 5.29 (m, 1H), 5.18–4.89 (m, 4H), 4.72 (m, 1H), 4.13 (m, 1H), 3.00 (m, 2H), 1.66–1.29 (m, 3H), 0.89 (m, 6H); FABMS m/z (562, MH+).

EXAMPLE 11

1-[N-[N-Benzyloxycarbonyl-L-leucyl]-3S-4-phenyl-3-amino-2-oxobutyloxy]-6'-chloro-5'-methylbenzotriazole.

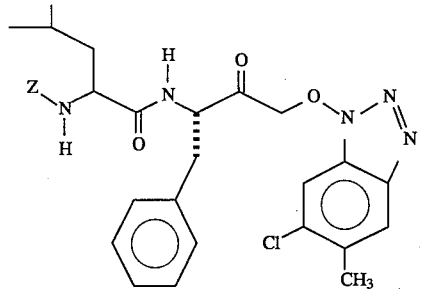

Method A; reaction time: 15.5 h; yield 37%; purification: HPLC (reverse phase, acetonitrile :water (containing 0.1% trifluoroacetic acid) 10%–100% over 40 min) $R_t$: 32.53 min; $^1$H NMR (300 MHz, CDCl$_3$): δ7.87 (s, 1H), 7.83 (s, 1H), 7.43–6.92 (m, 10H), 6.58 (m, 1H), 5.26 (m, 1H), 5.15–4.89 (m, 4H), 4.72 (m, 1H), 4.12 (m, 1H), 2.98 (m, 2H), 2.53 (s, 3H), 1.63–1.32 (m, 3H), 0.89 (m, 6H), FABMS m/z (592, MH+).

EXAMPLE 12

1-[N-[N-Benzyloxycarbonyl-L-leucyl]-3S-4-phenyl-3-amino-2-oxobutyloxy]-4'-methylbenzotriazole.

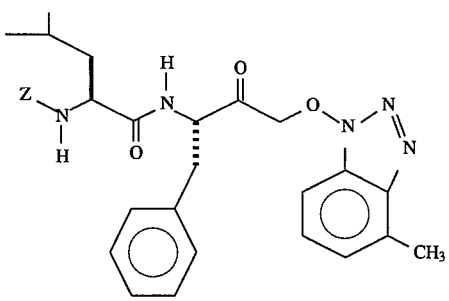

Method A; reaction time: 15.5 h; yield 15%; purification: HPLC (reverse phase, acetonitrile :water (containing 0.1% trifluoroacetic acid) 10%–100% over 40 min) $R_t$: 32.63 min; $^1$H NMR (300 MHz, CDCl$_3$): δ7.61 (d, 1H), 7.52–6.92 (m, 12H), 6.55 (m, 1H), 5.26 (m, 1H), 5.15–4.92 (m, 4H), 4.80 (m, 1H), 4.10 (m, 1H), 3.03 (m, 2H), 2.76 (s, 3H), 1.8–1.34 (m, 3H), 0.89 (m, 6H), FABMS m/z (558, MH+).

EXAMPLE 13

1-[N-[N-Benzyloxycarbonyl-L-leucyl]-3S-4-phenyl-3-amino-2-oxobutyloxy]-5'-chloro-6'-methylbenzotriazole.

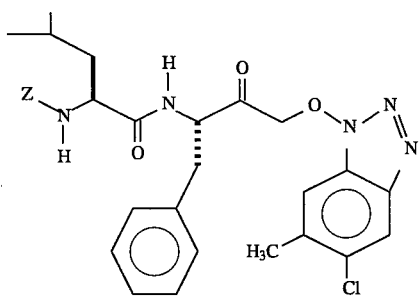

Method A; reaction time: 15 h; yield 25%; purification: HPLC (reverse phase, acetonitrile:water (containing 0.1% trifluoroacetic acid) 10%–100% over 40 min) $R_t$: 34.06 min; $^1$H NMR (300 MHz, CDCl$_3$): δ8.00 (s, 1H), 7.70 (s, 1H), 7.43–6.93 (m, 10H), 6.58 (m, 1H), 5.29 (m, 1H), 5.15–4.90 (m, 4H), 4.73 (m, 1H), 4.10 (m, 1H), 2.97 (m, 2H), 2.58 (s, 3H), 1.66–1.30 (m, 3H), 0.89 (m, 6H); FABMS m/z (592, MH+).

EXAMPLE 14

1-[N-[N-Benzyloxycarbonyl-L-leucyl]-3S-4-phenyl-3-amino-2-oxobutyloxy]-4'-chlorobenzotriazole.

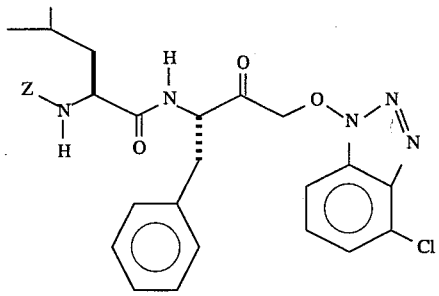

Method A; reaction time: 3 h; yield 19%; purification: HPLC (reverse phase, acetonitrile:water (containing 0.1% trifluoroacetic acid) 10%–100% over 40 min) $R_t$: 32.13 min; $^1$H NMR (300 MHz, CDCl$_3$): δ7.75 (d, 1H), 7.49–6.86 (series of m, 12H), 6.59 (m, 1H), 5.29 (m, 1H), 5.12–4.89 (m, 4H), 4.66 (m, 1H), 4.09 (m, 1H), 2.96 (m, 2H), 1.66–1.29 (m, 3H), 0.89 (m, 6H); FABMS m/z (578, MH+).

EXAMPLE 15

1-[N-[N-Benzyloxycarbonyl-L-leucyl]-3S-4-phenyl-3-amino-2-oxobutyloxy]-6'-phenylbenzotriazole.

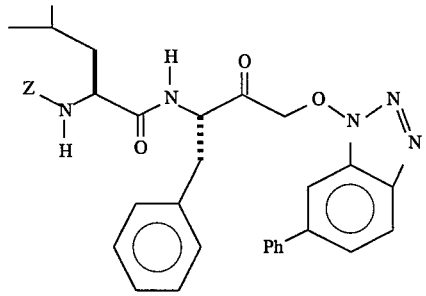

Method A; reaction time: 15 h; yield 3%; purification: HPLC (reverse phase, acetonitrile:water (containing 0.1% trifluoroacetic acid) 10%–100% over 40 min) $R_t$: 33.23 min; $^1$H NMR (300 MHz, CDCl$_3$): δ8.02 (m, 2H), 7.79–6.94 (series of m, 16H), 6.63 (m, 1H), 5.30 (bd, 1H), 5.15–4.9 (m, 4H), 4.77 (m, 1H), 4.12 (m, 1H), 3.00 (m, 2H), 1.7–1.3 (series of m, 3H), 0.87 (m, 6H); FABMS m/z (620, MH+).

EXAMPLE 16

1-[N-[N-Benzyloxycarbonyl-L-leucyl]-3S-4-phenyl-3-amino-2-oxobutyloxy]-4',5',6',7'-tetrafluorobenzotriazole.

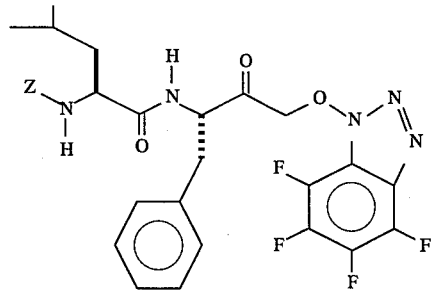

Method A; reaction time: 15 h; yield 4%; purification: HPLC (reverse phase, acetonitrile:water (containing 0.1% trifluoroacetic acid) 10%–100% over 40 min) $R_t$: 33.08 min; $^1$H NMR (300 MHz, CDCl$_3$): δ7.43–7.00 (m, 10H), 6.57 (m, 1H), 5.35 (bd, 1H), 5.1–4.89 (s overlapping with m, 4H), 4.70 (m, 1H), 4.12 (m, 1H), 3.03 (m, 2H), 1.7–1.2 (m, 3H), 0.92 (m, 6H); FABMS m/z (616, MH+).

EXAMPLE 17

1-[N-[N-Benzyloxycarbonyl-L-leucyl]-3S-4-phenyl-3-amino-2-oxobutyloxy]-5'-chlorobenzotriazole.

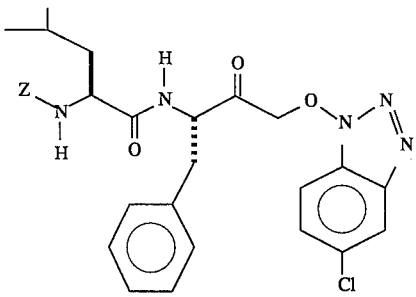

Method A; reaction time: 3 h; yield 58%; purification: HPLC (reverse phase, acetonitrile:water (containing 0.1% trifluoroacetic acid) 10%–100% over 40 min) $R_t$: 30.36 min; $^1$H NMR (300 MHz, CDCl$_3$): δ8.00 (s, 1H), 7.83 (d, 1H), 7.52 (d, 1H), 7.44–6.9 (m, 10H), 6.63 (m, 1H), 5.30 (bd, 1H), 5.15–5.00 (s and m, 4H), 4.90 (m, 1H), 4.12 (m, 1H), 2.97 (m, 2H), 1.66–1.35 (m, 3H), 0.90 (m, 6H); FABMS m/z (578, MH+).

The following Examples of the compounds listed in Table IA were prepared in a manner similar to that for Example 17.

EXAMPLE 18

1-[N-[N-Benzyloxycarbonyl-L-leucyl]-3S-4-phenyl-3-amino-2-oxobutyloxy]-5',6'-dichlorobenzotriazole.

$R_t$:31.85 min; $^1$H NMR (300 MHz, CDCl$_3$): δ8.12 (s, 1H), 8.04(s, 1H), 7.40–6.88 (m, 10H), 6.68 (m, 1H), 5.30 (m, 1H), 5.16–4.88(s and m, 4H), 4.64 (m, 1H), 4.12 (m, 1H), 3.00 (m, 2H), 1.66–1.3 (m, 3H), 0.92 (m, 6H); FABMS M/Z (614, mh+).

EXAMPLE 19

1-[N-[N-Benzyloxycarbonyl-L-leucyl]-3S-4-phenyl-3-amino-2-oxobutyloxy]-(1H)-triazolo[4,5-b]pyridine.

$R_t$:27.24 min; $^1$H NMR (300 M}{z, CDCl$_3$): δ8.8 (m, 1H), 8.37 (m, 1H), 7.54 (m, 1H), 7.43–6.89 (m, 10H), 6.80 (m, 1H), 5.40 (m, 1H), 5.23–4.97 (s and m, 4H), 4.66 (m, 1H), 4.14 (m, 1H), 2.97 (m, 2H), 1.66–1.32 (m, 3H), 0.88 (m, 6H); FABMS m/z (545, MH+).

EXAMPLE 20

1-[N-[N-Benzyloxycarbonyl-L-leucyl]-3S-4-phenyl-3-amino-2-oxobutyloxy]-4',5',6',7'-tetrachlorobenzotriazole.

$R_t$:34.67 min $^1$H NMR (300 MHz, CDCl$_3$): δ7.40–7.06 (m, 10H), 6.63 (m, 1H), 5.32 (m, 1H), 5.14–4.91(s and m, 4H), 4.86(m, 1H), 4.10 (m, 1H), 3.08(m, 2H), 1.49–1.2 (m, 3H), 0.89 (m, 6H); FABMS m/z (682, MH+).

EXAMPLE 21

1-[N-[N-Benzyloxcarbonyl-L-leucyl]-3S-4-phenyl-3-amino-2-oxobutyloxy]-4',6',7'-trichlorobenzotriazole.

$R_t$:33.56 min; $^1$H NMR (300 MHz, CDCl$_3$): δ7.52 (s, 1H), 7.43–7.00 (m, 10H), 6.57 (m, 1H), 5.28(bd, 1H), 5.17–4.83(m, 5H), 4.11 (m, 1H), 3.08 (m, 2H), 1.63–1.2 (m, 3H), 0.85 (m, 6H); FABMS m/z (648, MH+).

EXAMPLE 22

1-[N-[N-Benzyloxycarbonyl-L-leucyl]-(3S)-4-phenyl-3-amino-2-oxobutyloxy]benzimidazole.

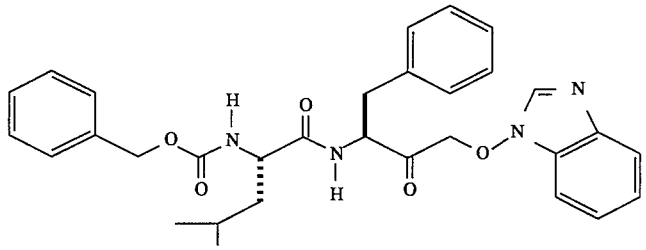

Method B, reaction time 40 min; purification: HPLC (reverse phase, acetonitrile:water (containing 0.1% trifluoroacetic acid) 10%–100% over 40 min.) $R_t$: 24.64 min; yield 41%; $^1$H NMR (300 MHz, CDCl$_3$): δ9.14 (br, 1H), 7.81 (m, 1H), 7.6–7.0 (m, 16H), 5.5–4.9 (m, 3H), 4.59 (m, 1H), 4.10 (m, 1H), 3.00 (m, 2H), 1.53 (m, 1H), 1.40 (m, 2H), 0.83 (2d, 6H); FABMS m/z 543 (MH$^+$); mp 56–60 C.

EXAMPLE 23

1-[N-[N-Benzyloxycarbonyl-L-leucyl]-3S-4-phenyl-3-amino-2-oxobutyloxy]-4',5'-dichlorobenzotriazole.

$R_t$:32.70 min; $^1$H NMR (300 MHz, CDCl$_3$ ): δ7.63 (d, 1H), 7.46 (d, 1H), 7.32–6.75 (m, 10H), 6.53 (m, 1H), 5.20 (m, 1H), 5.03–4.8 (s and m, 4H), 4.50 (m, 1H), 3.97(m, 1H), 2.80 (m, 2H), 1.45–1.14 (m, 3H), 0.80 (m, 6H); FABMS m/z (614, MH+).

EXAMPLE 24

1-[N-[N-Benzyloxycarbonyl-L-leucyl]-3S-4-phenyl-3-amino-2-oxobutyloxy]-5'-chloro-6'-ethylbenzotriazole.

$R_t$:33.90; $^1$H NMR (300 MHz, CDCl$_3$): δ7.91(s, 1H), 7.63 (s, 1H), 7.32–6.85 (m, 10H), 6.57(m, 1H), 5.23 (m, 1H), 5.06–4.86(s and m, 4H), 4.66 (m, 1H), 4.03 (m, 1H), 3.03–2.8 (m, 4H), 1.57–1.2 (m and t, 6H), 0.80 (m, 6H); FABMS m/z (606, MH+).

EXAMPLE 25

1-[N-[N-Benzyloxycarbonyl-L-leucyl]-3S-4-phenyl-3-amino-2-oxobutyloxy]-4',5'-difluorobenzotriazole.

$R_t$:31.54 min; $^1$H NMR (300 MHz, CDCl$_3$): δ7.63(m, 1H), 7.51–690(m, 11H), 6.68 (m, 1H), 5.34 (m, 1H), 5.2–4.92 (s and m, 4H), 4.67 (m, 1H), 4.09 (m, 1H), 2.97 (m, 2H), 1.66–1.31 (m, 3H), 0.92 (m, 6H); FABMS m/z (580, MH+).

EXAMPLE 26

1-[N-[N-Benzyloxycarbonyl-L-leucyl]-3S-4-phenyl-3-amino-2-oxobutyloxy]-6'-methylbenzotriazole.

$R_t$:31.57 min; $^1$H NMR (300 MHz, CDCl$_3$ ); δ7.88 (d, 1H), 7.57 (s, 1H), 7.43–6.94(m, 11H0, 6.67 (m, 1H), 5.25 (d, 1H), 5.11–4.92 (s and m, 4H), 4.80(m, 1H0, 4.11 (m, 1H, 3.03 (m, 2H), 2.59(s, 3H), 1.66–1.3 (m, 3H), 0.90 (m, 6H); FABMS m/z (558, MH+).

EXAMPLE 27

1-[N-[N-Benzyloxycarbonyl-L-leucyl]-3S-4-phenyl-3-amino-2-oxobutyloxy]-5'-methylbenzotriazole.

$R_t$: 31.59 min; $^1$H NMR (300 MHz, CDCl$_3$): δ7.74 (m, 2H), 7.43–694 (m, 11H), 6.68 (m, 1H), 5.27 (bd, 1H), 5.14–4.91 (s and m, 4H), 4.74 (m, 1H), 4.11 (m, 1H), 3.00 (m, 2H), 2.52 (s, 3H), 1.68–1.3 (m, 3H), 0.86 (m, 6H); FABMS m/z (558, MH+).

EXAMPLE 28

1-[N-[N-Benzyloxycarbonyl-L-leucyl]-3S-4-phenyl-3-amino-2-oxobutyloxy]-3-benzotriazin-4-one.

Method B. reaction time 4 h; purification, recrystallization (EtOAc/Hexanes); yield 76%1; mp 155°–157° C.; $^1$H-NMR (300 MHz, CDCl$_3$): δ8.38 (d, 5 Hz, 1H), 8.22 (d, 5 Hz, 1H), 8.01 (d, 5 Hz, 1H), 7.85 (d, 5 Hz, 1H), 7.35–7.15 (m, 10H), 6.95 (m, 1H), 5.20–4.90 (m, 6H), 4.20–4.10 (m, 1H), 3.40–3.30 (m, 1H), 3.20–3.05 (m, 1H), 1.65–1.35 (m 3H), 0.95–0.85 (m, 6H); MS (ESI): 572 (M+H)+; Anal, calcd for C$_{31}$H$_{33}$N5O$_6$; C (65.12), H (5.83), N (12.25); Fd: C (65.06), H (5.74), N (12.39).

EXAMPLE 29

1-[N-[N-Benzyloxycarbonyl-L-leucyl]-3S-4-Phenyl-3-amino-2-oxobutyloxy]-3-(6',7'-dimethoxy)benzotriazin-4-one.

Method B. reaction time 5 h; purification, recrystallization (EtOAc/Hexanes); yield 73%; mp 180°–185° C.(dec); $^1$H-NMR (300 MHz, CDCl$_3$): δ7.61 (s, 1H), 7.52 (s, 1H), 7.35–7.15 (m, 10H), 6.90 (m, 1H), 5.20–4.80 (m, 6H), 4.22–4.10 (m, 1H), 4.05 (2d, 6H), 3.40–3.30 (m, 1H), 3.18–3.05 (m, 1H), 1.65–1.35 (m, 3H), 0.95–0.85 (m, 6H); MS (ESI): 632 (M+H)+; Anal, calcd for C$_{33}$H$_{37}$N$_5$O$_8$; C(62.74), H(5.92), N(11.09); Fd: C(62.51), H(5.76), N(11.03).

EXAMPLE 30

1-[N-[N-Benzyloxycarbonyl-L-leucyl]-3S-4-phenyl-3-amino-2-oxobutyloxy]-3-(6'-chloro)benzotriazin-4-one.

Method B. reaction time 4 h; purification, recrystallization (EtOAc/Hexanes); yield 57%; mp 150°–153° C. (dec); $^1$H-NMR (300 MHz, CDCl$_3$): δ8.35 (s, 1H), 8.15 (d, 5 Hz, 1H), 7.92 (d, 5 Hz, 1H), 7.35–7.15 (m, 10H), 6.90 (m, 1H), 5.15–4.85 (m, 6H), 4.20–4.10 (m, 1H), 3.35–3.25 (m, 1H), 3.15–3.05 (m, 1H), 1.65–1.35 (m 3H), 0.95–0.85 (m, 6H); MS (ESI): 607/609 (M+H)+; mono-chloro isotope pattern; Anal, calcd for C$_{31}$H$_{32}$N$_5$O$_{6Cl}$: C(61.42), H(5.33), N(11.56), Cl(5.85); Fd: C(61.34), H(5.33), N(11.54), Cl(6.20).

EXAMPLE 31

1-[N-[N-Benzyloxycarbonyl-L-leucyl]-3S-5-methyl-3-amino-2-oxohexyloxy]-3-benzotriazin-4-one.

Method B. reaction time 21 h; purification, recrystallization (EtOAc/Hexanes); yield 52%; mp 147°–148.5° C.; $^1$H-NMR (300 MHz, CDCl$_3$): δ8.38 (d, 5 Hz, 1H), 8.22 (d, 5 Hz, 1H), 8.01 (d, 5 Hz, 1H), 7.85 (d, 5 Hz, 1H), 7.35 (m, 5H), 6.80 (m, 1H), 5.20–4.95 (m, 6H), 4.30–4.20 (m, 1H), 1.90–1.50 (m, 6H), 1.00–0.90 (m, 12H); MS (ESI): 538 (M+H)+; Anal, calcd for C$_{28}$H$_{35}$N$_5$O$_6$; C (62.54), H6.58), N(13.03); Fd: C(62.43), H(6.52), N(12.96).

Synthesis of Compounds Containing Xanthene-9-yl and 1-phenylpropyl Functionality Synthesis of compounds containing the xanthen-9-yl and 1-phenylpropyl functionality are depicted in Scheme 2.

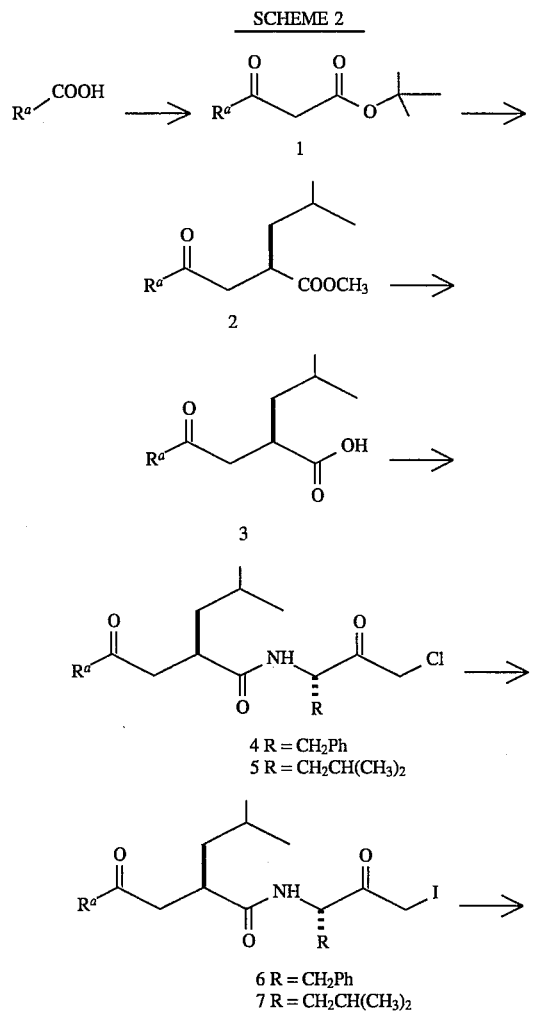

SCHEME 2

-continued
SCHEME 2

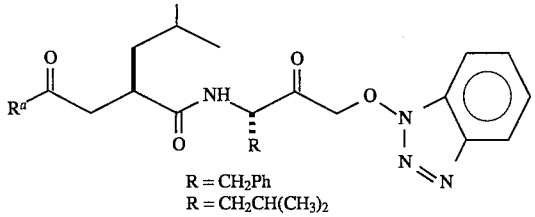

R = CH₂Ph
R = CH₂CH(CH₃)₂

EXAMPLE 32

Synthesis of Intermediate 1 (Scheme 2):

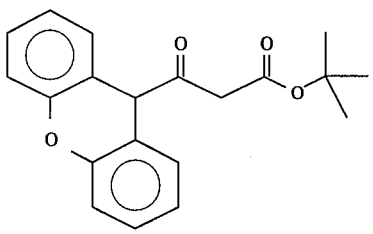

To a cooled (0° C.) solution of xanthene-9-carboxylic acid (9.05 g, 0.04 mole) in anhydrous THF (40 mL) was added 1,1'-carbonyldiimidazole (6.81 g, 0.042 mole). The mixture was stirred at 0° C. for 0.5 h and then at room temperature overnight. The next day, this solution was added slowly, over 1 h, to a cooled (–78° C.) solution of tert-butyl lithioacetate (0.088 mole, generated, in situ from tert-butyl acetate and lithium diisopropylamide) in THF (40 mL) hexane (35 mL). The mixture was stirred for an additional 0.5 h, quenched with 1N HCl (88 mL), brought to 0° C. and acidified with 1N HCl to pH 3–4. The resulting aqueous solution was extracted with ethyl acetate (2×100 mL). The organic layer was washed with brine, dried over anhydrous sodium sulfate, and the solvent was removed under reduced pressure. Purification by flash chromatography (silica gel, 6% ethyl acetate-hexane) gave 8.7 g of the desired product: ¹H-NMR (300 MHz, CDCl₃) δ7.40–7.00 (m, 8H), 5.00 (s, 1H), 3.20 (s, 1H) 1.40 (s, 9H). A general description of this procedure can be found in Harris, B. D. et al., *Tetrahedron Lett.* 28(25) 2837 (1987), and in Hamada, Y. et al., *J. Am. Chem. Soc.* 111, 669 (1989).

EXAMPLE 33

Synthesis of Intermediate 2 (Scheme 2):

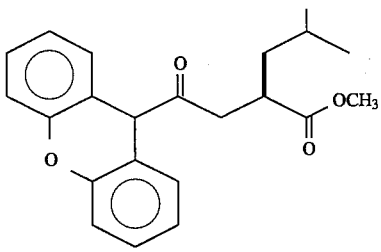

To a stirred slurry of 60% sodium hydride in oil (0.860 g, 0.0215 mol) in anhydrous THF (10 mL), was added slowly the keto ester Intermediate 1 (6.63 g, 0.02 mol) in anhydrous THF (20 mL). After the evolution of hydrogen gas ceased, the solution was treated with 6.82 g of the leucine-triflate methyl ester {generated from the corresponding (D)-hydrox-yester (4.00 g) and triflic anhydride (8.05 g) in the presence of 2,6-lutidine (3.06 g)} adapted from the procedure described in Hoffman, R. V. et al., *Tetrahedron Lett.* 34(13), 2051 (1993). The resulting mixture was stirred overnight, diluted with ether (100 mL) washed with water (30 mL) and concentrated under reduced pressure to give 7.00 g of crude diester intermediate. This material was then dissolved in trifluoroacetic acid (TFA, 7 mL) and stirred at room temperature for 1 hr. The TFA was removed and the residue dissolved in benzene (30 mL) and heated at reflux for 1 h. The solvent was removed under reduced pressure and purification by flash chromatography (silica gel, 4% ethyl acetate-hexane) gave 2.34 g of the product, Intermediate 2: ¹H NMR (300 MHz, CDCl₃) δ7.40–7.0 (m, 8H), 4.90 (s,1H), 3.55 (s,3H), 2.80–2.60 (m, 2H), 2.30 (dd, J=8 Hz and 2 Hz, 1H), 1.30 (m, 2H), 1.00 (m, 1H), 0.80 (d,J=8 Hz, 3H), 0.70 (d,J=8 Hz, 3H).

EXAMPLE 34

Intermediate 3 (Scheme 2):

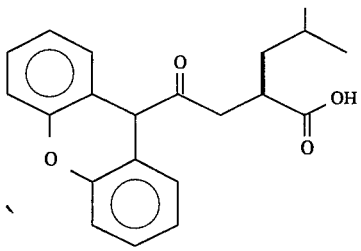

A mixture of Intermediate 2 (2.33 g, 6.6 mmol) lithium hydroxide-monohydrate (0.360 g), methanol (27 mL), and water (9 mL), was heated at 70°–75° C. for 1.5 h. The methanol was removed under reduced pressure. The resulting aqueous solution was washed with diethyl ether (20 mL), acidified at 0° C. with 1N HCl and then extracted with diethyl ether (3×10 mL). The organic layer was washed once with brine and dried over anhydrous sodium sulfate. Filtration followed by removal of the solvent under reduced pressure produced 1.83 g of the product, Intermediate 3. ¹H-NMR (300 MHz, CDCl₃) δ7.40–7.00 (m, 8H), 4.95 (s,1H), 2.80–2.60 (m, 2H), 2.30 (dd, J=8 Hz and 2 Hz, 1H), 1.35 (m, 1H), 1.00 (m, 1H), 0.80 (d, J=8 Hz, 3H), 0.70 (d, J=8 Hz, 3H).

EXAMPLE 35

Intermediate 4 (Scheme 2):

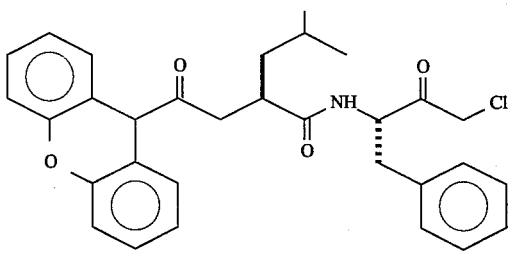

To a cooled (–60° C.) solution of Intermediate 3 [0.148 g, 0.4373 mmol] in anhydrous THF (3 mL) was added N-methylmorpholine (0.142 g) followed by isobutyl chloroformate (0.066 g). The mixture was stirred for 0.5 h and the cooling bath replaced by an ice-water bath. To the reaction mixture was added 0.012 g of phenylalanine chloromethyl ketone hydrochloride in DMF (3 mL). The resulting mixture was stirred at 0° C. for 1 h then at room temperature overnight. The mixture was then diluted with ethyl acetate (20 mL), washed with 2% aqueous citric acid (2–10 mL), 2% aqueous NaHCO$_3$ (2×10 mL), brine (1×10 mL), and dried over anhydrous sodium sulfate. Filtration and removal of the solvent under reduced pressure gave crude Intermediate 4. Purification by flash chromatography (silica gel, 15% ethyl acetatehexane) afforded 0.105 g of Intermediate 4. $^1$H-NMR (300 MHz, CDCl3), δ7.10–7.30 (m, 13H), 6.15 (d, J=6 Hz, 1H), 4.90 (s, 1H), 4.70 (q, J=6 Hz, 1H), 4.05 (d, J=16 Hz, 1H), 3.85 (d, J=16 Hz, 1H), 3.00 (m, 1H), 2.50 (m, 2H), 2.30 (dd, J=8 Hz and 2 Hz, 1H), 1.30 (m, 2H), 0.90 (m, 1H), 0.75 (d, J=6 Hz,3H), 0.65 (d, J=6 Hz, 3H).

EXAMPLE 36

Intermediate 5 (Scheme 2):

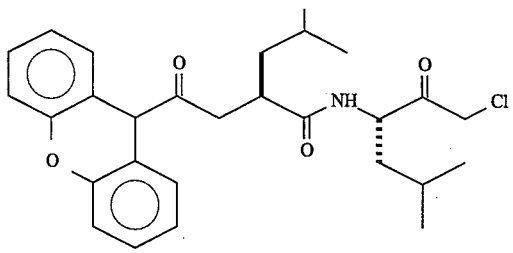

Following the same procedure described for the synthesis of Intermediate 4, Intermediate 3 [0.408 g, 1.205 mmol] was coupled with leucine chloromethyl ketone hydrochloride (0.241 g) to yield 5 (0.146 g): $^1$H-NMR (300 MHz, CDCl$_3$) δ7.40–7.00 (m, 8H), 6.00 (d, J=8 Hz, 1H), 4.90 (s, 1H), 4.60 (m, 1H), 4.20 (s, 2H), 2.70–2.50 (m, 2H), 2.35 (dd, J=8 Hz and 2 Hz, 1H), 1.60–1.20 (m, 4H), 0.95 (d, J=8 Hz, 3H), 0.90 (m, 2H), 0.85 (d, J=8 Hz, 3H), 0.80 (d, J=8 Hz, 3H), 0.70 (d, J=8 Hz, 3H).

EXAMPLE 37

Intermediate 6 (Scheme 2)

A mixture of Intermediate 4 (0.030 g, 0.058 mmol), sodium iodide (0.022 g) and acetone (3 mL) was stirred at room temperature for 1 h. The solvent was removed under reduced pressure and the residue was partitioned between H$_2$O (5 mL) and CH$_2$Cl$_2$ (2×5 mL). The organic layer was dried over anhydrous sodium sulfate, filtered, and the solvent removed under reduced pressure, to give 0.036 g of Intermediate 6: $^1$H-NMR (300 MHz, CDCl$_3$) δ7.40–7.00 (m, 13H), 6.15 (d, J=6 Hz, 1H), 4.90 (s, 1H), 4.85 (q, J=6 Hz, 1H), 3.70 (d, J=8 Hz, 1H), 3.60 (d, J=8 Hz, 1H), 3.00 (m, 2H), 2.50 (m, 2H), 2.30 (dd, J=8 Hz and 2 Hz, 1H), 1.30 (m, 2H), 0.85 (m, 1H), 0.75 (d, J=6 Hz, 3H), 0.65 (d, J=6 Hz, 3H).

EXAMPLE 38

Intermediate 7 (Scheme 2):

Following the same procedure described for the synthesis of Intermediate 6, Intermediate 5 (0.105 g, 0.217 mmol) was converted to Intermediate 7 (0.120 g): 1H-NMR (300 MHz, CDCl$_3$) δ7.40–7.00 (m, 8H), 6.00 (d, J=8 Hz, 1H), 4.90 (s, 1H), 4.70 (m, 1H), 3.90 (d, J=6 Hz, 1H), 3.85 (d, J=6 Hz, 1H), 2.70–2.50 (m, 2H), 2.35 (dd, J=8 Hz and 2 Hz, 1H), 1.60–1.20 (m, 4H), 0.95 (d, J=8 Hz, 3H), 0.90 (m, 2H), 0.85 (d, J=8 Hz, 3H), 0.80 (d, J=8 Hz, 3H), 0.75 (d, J=8 Hz, 3H).

EXAMPLE 39

1-[N-[2-(2-Methylpropyl)-1,4-dioxo-4-(xanthen-9-yl)butyl]-3S-3-amino-2-oxo-4-phenylbutyloxy]benzotriazole.

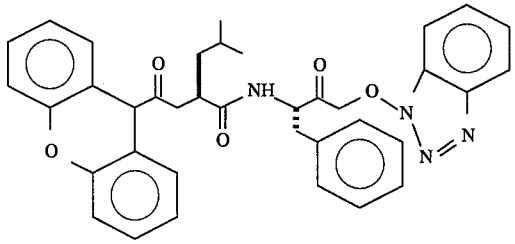

Using method A, Intermediate 6 (0.046 g, 0.075 mmol) was coupled with 1-hydroxybenzotriazole (0.014 g) to give the product (0.046 g) as a white solid after purification by crystallization from ethyl acetate-hexane: mp 99°–101° C.; FABMS 618 m/z (MH$^+$); $^1$ HNMR (300 MHz, CDCl$_3$) δ8.00 (d, J=6 Hz, 1H), 7.80 (d, J=6 Hz, 1H), 7.70 (t, J=6 Hz, 1H), 7.00 (t, J=6 Hz, 1H), 7.30–6.90 (m, 13H), 6.10 (d, J=8 Hz, 1H), 5.15 (d, J=16 Hz, 1H), 4.90 (d, J=16 Hz, 1H), 4.85 (s, 1H), 4.55 (m, 1H), 2.90 (m, 2H), 2.50 (m, 2H), 2.30 (dd, J=8 Hz and 2 Hz, 1H), 1.30 (m, 2H), 0.85 (m, 1H), 0.75 (d, J=6 Hz, 3H), 0.65 (d, J=6 Hz, 3H).

EXAMPLE 40

1-[N[-[2-(2-Methylpropyl)-1,4-dioxo-4-(xanthen-9-yl)butyl]-3S-3-amino-5-methyl-2-oxohexyloxy]benzotriazole.

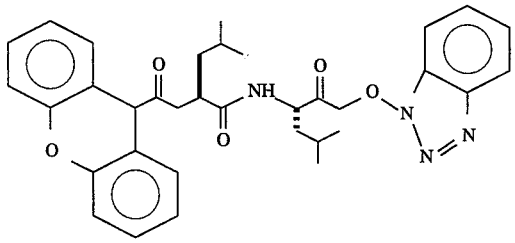

Using method A, Intermediate 7 (0.115 g, 0.2 mmol)was coupled with 1-hydroxybenzotriazole (0.034 g) to give the compound (0.051 g) as a white solid: m.p. 92°–94° C.; $^1$H-NMR (300 MHz, CDCl$_3$); δ8.00 (d, J=6 Hz, 1H), 7.80 (d, J=6 Hz, 1H), 7.65 (t, j=7 Hz, 1H), 7.40 (t, J=7 Hz, 1H), 7.35–7.00 (m, 8H), 6.00 (d, J=8 Hz, 1H), 5.40, (s, 2H), 4.90 (s, 1H), 4.50 (m, 1H), 2.70–2.50 (m, 2H), 2.30 (dd, J=8 Hz and 2H, 1H), 1.60–1.20 (m, 4H), 0.95 (d, J=8 Hz, 3H), 0.90 (m, 2H), 0.85 (t, J=8 Hz, 3H), 0.80 (d, J=8 Hz, 3H), 0.75 (d, J=8 Hz, 3H).

EXAMPLE 41

Synthesis of Intermediate 1a ( Scheme 2)

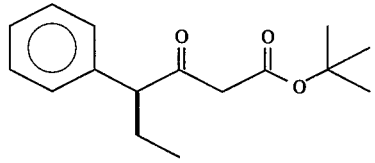

Following the same method for the synthesis of the Intermediate 1 of Example 32 (R$^a$=9-xanthenyl), (S)–(+)–2-phenylbutyric acid (3.93 g, 0.024 mole) was converted to Intermediate 1a, R$^a$=1-phenylpropyl (4.13 g): $^1$HNMR (300

MHz, CDCl₃) δ:7.38–7.18 (m, 5H), 3.70 (t, J=6 Hz, 1H), 3.35 (d, J=16 Hz, 1H), 3.20 (d, J=16 Hz, 1H), 2.10 (m, 1H), 2.70 (m, 1H), 1.45 (s, 9H), 0.85 (t, J=17 Hz, 3H).

EXAMPLE 42

Synthesis of Intermediate 2a (Scheme 2)

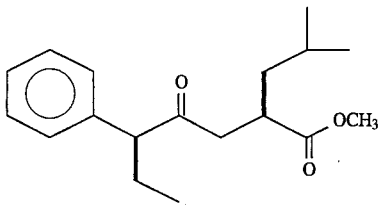

Following the same method for the synthesis of the Intermediate 2 of Example 33, ($R^a$=9-xanthenyl), Intermediate 1a (3.25 g, 0.0124 mole) was converted to Intermediate 2a (2.85 g): ¹HNMR (300 MHz, CDCl₃) δ7.40–7.18 (m, 5H), 3.60 (S, 3H), 3.50 (t, J=6 Hz, 1H), 2.85 (m, 1H), 2.75 (m, 1H), 2.45 (dd, J=18 Hz and 2 Hz, 1H), 2.05 (m, 1H), 1.70 (m, 1H), 1.45 (m, 2H), 1.15 (m, 1H), 0.90–0.70 (m, 9H).

EXAMPLE 43

Synthesis of Intermediate 3a (Scheme 2)

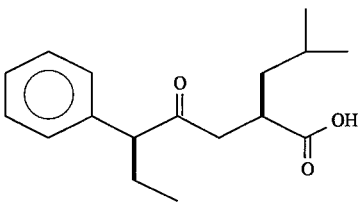

Intermediate 2a (0.570 g, 1.963 mmol) was hydrolyzed to Intermediate 3a ($R^a$=1-phenylpropyl) (0.507 g), following the same procedure for the synthesis of Intermediate 3 of Example 34 ($R^a$=9-xanthenyl): ¹HNMR (300 MHz, CDCl₃) δ:7.40–7.10 (m, 5H), 3.60 (m, 1H), 2.90 (m, 1H), 2.75 (m, 1H), 2.50 (m, 1H), 2.05 (m, 1H), 1.70 (m, 1H), 1.50 (m, 2H), 1.15 (m, 1H), 0.90–0.70 (m, 9H).

EXAMPLE 44

Synthesis of Intermediate 4a (Scheme 2)

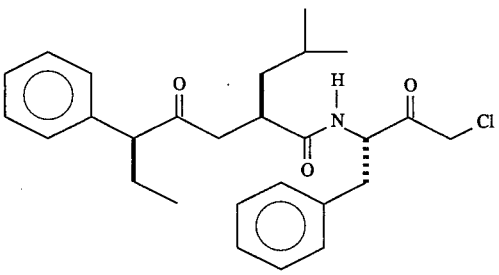

Following the same procedure for the synthesis of Intermediate 4 of Example 35 ($R^a$=9-xanthenyl, R=benzyl), Intermediate 3a (0.386 g, 1.40 mmol) was converted to Intermediate 4a ($R^a$=1-phenylpropyl, R=benzyl) (0.382 g, 72.28 diastereomeric mixture): ¹HNMR (300 MHz, CDCl₃) δ7.40–7.10 (m, 10H), 6.30 (d, J=6 Hz, 1H), 4.85 and 4.75 (2 set of q, 72:28, J=6 Hz, 1H), 4.10 and 4.05 (2 sets of doublet, 72:28, J=18 Hz, 1H), 3.90 and 3.85 (2 sets of doublet, 72:28, J=18 Hz, 1H), 3.50 (m, 1H), 3.10 (m, 1H), 2.95 (m, 1H), 2.65 (m, 2H), 2.40 (m, 1H), 2.00 (m, 1H), 1.70 (m, 1H), 1.35(m, 2H), 1.00 (m, 1H), 0.90–0.65 (m, 9H).

EXAMPLE 45

Synthesis of Intermediate 5a (Scheme 2)

0.087 g (0.1907 mmol) of Intermediate 4a, $R^1$=1-phenylpropyl, R=benzyl, was converted to Intermediate 5a ($R^a$=1-phenylpropyl, R=benzyl) (0.094 g, 72:28 diastereomeric mixture) following the same procedure for the synthesis of Intermediate 6 of Example 36, ($R^a$=9-xanthenyl, R=benzyl): ¹HNMR (300 MHz, CDCl₃) δ7.40–7.10 (m, 10H), 6.30 (mixture of doublets, 1H), 5.00 and 4.85 (2 sets of quartets, 72:28, J=6 Hz, 1H), 3.75 and 3.65 (2 sets of doublets, 72:28, J=16 Hz, 1H), 3.70 and 3.60 (2 sets of doublets, 72:28, J=16 Hz, 1H), 3.50 (m, 1H), 3.10 (d, J=6 Hz, 1H), 3.00 (m, 1H), 2.65 (m, 2H), 2.40 (m, 1H), 2.00 (m, 1H), 1.70 (m, 1H), 1.40 (m, 2H), 1.00 (m, 1H), 0.85–0.70 (m, 9H).

EXAMPLE 46

1-[N-[2R-(2-methylpropyl)-1,4-dioxo-5S-phenylheptan-1-yl]-3S-3-amino-2-oxo-4-phenylbutyloxy]benzotriazole

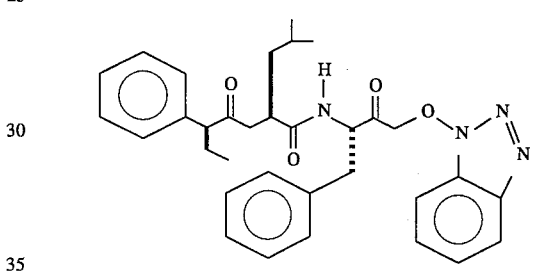

Following method A, Intermediate 5a, (0.094 g, 0.1716 mmol) was coupled with 1-hydroxybenzotriazole (0.030 g) to give 1-[N-[2R-(2-methylpropyl)-1,4 -dioxo- 5S-phenylheptan-1-yl]-3S -3-amino-2-oxo-4-phenylbutyloxy]benzotriazole (0.080 g) as a mixture (72:28) of diastereomers: ¹HNMR (300 MHz, CDCl₃) δ8.00 (d, J=6 Hz, 1H), 7.85 and 7.80 (2 sets of doublets, 72:28, J=6 Hz, 1H), 7.55 (t, J=6 Hz, 1H), 7.40 (t, J=6 Hz, 1H), 7.30–6.20 (m, 10H), 6.25 (mix. of doublets, 1H), 5.30 and 5.20 (2 sets of doublets, 72:28, J=16 Hz, 1H), 4.95 and 4.90 (2 sets of doublets, 72:28. J=6 Hz, 1H), 4.70 and 4.50 (2 sets of quartet, 72:28, J=7 Hz, 1H), 3.50 (m, 1H), 3.00 and 2.90 (2 sets of doublets, 72:28, J=8 Hz, 1H), 2.60 (m, 2H), 2.40 (m, 1H), 2.00 (m, 1H), 1.65 (m, 2H), 1.30 (m, 1H), 0.90 (m, 1H), 0.85–0.60 (m, 9H).

Each of the published documents mentioned in this specification is hereby incorporated by reference in their entirety.

Those skilled in the art will appreciate that numerous changes and modifications may be made to the preferred embodiments of the invention and that such changes and modifications may be made without departing from the spirit of the invention. It is therefore intended that the appended claims cover all equivalent variations as fall within the true spirit and scope of the invention.

What is claimed is:

1. A compound represented by the formula:

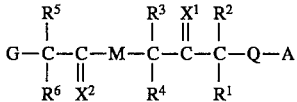

wherein:

M is selected from the group consisting of O, NR$^7$ and CR$^1$R$^2$;

X$^1$ is selected from the group consisting of O, S and NR$^7$;

X$^2$ is selected from the group consisting of O, S, NR$^7$ and two hydrogen atoms;

Q is selected from the group consisting of O, S and NR$^1$;

R$^1$ and R$^2$ are each independently selected from the group consisting of H, alkyl having from 1 to 10 carbons, heteroaryl having from 1 to 10 carbons, alkanoyl having from 1 to 10 carbons, and aroyl, wherein said alkyl, heteroaryl, alkanoyl and aroyl groups are optionally substituted with J;

R$^3$, R$^4$, R$^5$ and R$^6$ are each independently selected from the group consisting of H, alkyl having from 1 to 10 carbons, aryl, and heteroaryl, wherein said alkyl, aryl and heteroaryl groups are optionally substituted with J;

R$^7$ and R$^8$ are each independently selected from the group consisting of H, alkyl having from 1 to 10 carbons, aryl, and heteroaryl, wherein said alkyl, aryl and heteroaryl groups are optionally substituted with J;

J is selected from the group consisting of halogen, COOR$^7$, R$^7$OCO, R$^7$OCONH, OH, CN, NO$_2$, NR$^7$R$^8$, N=C(R$^7$)R$^8$, N=C(NR$^7$R$^8$)$_2$, SR$^7$, OR$^7$, phenyl, naphthyl, heteroaryl, and a cycloalkyl group having from 3 to 8 carbons;

G is selected from the group consisting of NH$_2$, NHR$^1$, CH$_2$R$^1$, CH$_2$C(O)B, carbobenzyloxy-NH, succinyl-NH, R$^7$O-succinyl-NH, R$^7$OC(O)NH, CH$_2$C(O)-(xanthen-9-yl), CH$_2$COR$^9$ wherein R$^9$ is selected from the group consisting of alkyl, aryl, and arylalkyl group of up to 13 carbons, and AA$^1$NHC(O)OCH$_2$C$_6$H$_5$ wherein AA$^1$ is selected from the group consisting of one of the 20 natural amino acids and an opposite antipode of said amino acid;

B is selected from the group consisting of alkyl having from 1 to 10 carbons, aralkyl having from 1 to 10 carbons, aryl having 1 to 3 carbocyclic rings, and heteroaryl having 1 to 3 rings, wherein said alkyl, aralkyl, aryl and heteroaryl groups are optionally substituted with J; and A is represented by the structure:

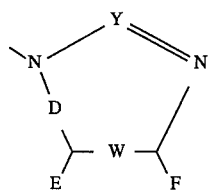

wherein:

Y is selected from the group consisting of N and CR$^1$;

W is selected from the group consisting of a double bond and a single bond;

D is a single bond;

E and F are each independently selected from the group consisting of R$^1$, R$^2$, J, and when E and F comprise a joined moiety, said moiety is selected from the group consisting of an aliphatic carbocyclic ring having from 5 to 7 carbons, an aromatic carbocyclic ring having from 5 to 7 carbons, an aliphatic heterocyclic ring having from 5 to 7 atoms, and an aromatic heterocyclic ring having from 5 to 7 atoms; wherein: said aliphatic heterocyclic ring and said aromatic heterocyclic ring each have from 1 to 4 heteroatoms; and said aliphatic carbocyclic ring, said aromatic carbocyclic ring, said aliphatic heterocyclic ring, and said aromatic heterocyclic ring are each optionally substituted with J.

2. The compound of formula 1 represented by the formula:

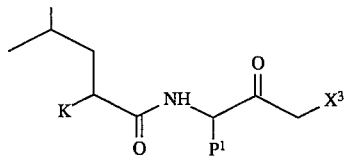

wherein:

K is selected from the group consisting of NHC(O)OCH$_2$C$_6$H$_5$, —CH$_2$C(O)-(xanthen-9-yl) and —CH$_2$C(O)CH(C$_6$H$_5$)C$_2$H$_5$;

p$^1$ is selected from the group consisting of isobutyl, isopropyl, benzyl, carboxyalkyl of 2–9 carbons and ethyl; and X$^3$ is represented by the structure:

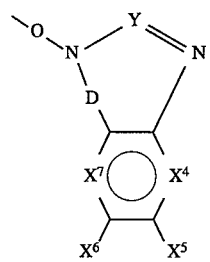

wherein:

D is a single bond;

X$^4$ is selected from the group consisting of CH, CCl, CCH$_3$, CF and N;

X$^5$ is selected from the group consisting of H, CH$_3$, Cl, OCH$_3$ and F;

X$^6$ is selected from the group consisting of H, CH$_3$, Cl, F, OCH$_3$, CF$_3$, ethyl and phenyl;

X$^7$ is selected from the group consisting of N, CCl, CH, COCH$_3$ and CF; and

Y is selected from the group consisting of N and CH.

3. The compound of claim 2 wherein K is —CH$_2$C(O)-(xanthen-9-yl)

4. The compound of claim 2 wherein P$^1$ is benzyl.

5. The compound of claim 4 wherein Y is N.

6. The compound of claim 4 wherein X$^3$ is O-1-oxybenzotriazole.

7. The compound of claim 2 wherein X$^7$ is N.

8. The compound of claim 2 wherein Y is CH.

9. The compound of claim 1 wherein Q is NR$^1$.

10. The compound of claim 1 wherein one of R$^1$ or R$^2$ is other than H.

11. The compound of claim 1 wherein X$^1$ is selected from the group consisting of S and NR$^7$.

12. The compound of claim 1 wherein neither of R$^3$ and R$^4$ are H.

13. The compound of claim 1 wherein M is selected from the group consisting of O and CR$^1$R$^2$.

14. The compound of claim 1 wherein X$^2$ is selected from the group consisting of S, NR$^7$, and two hydrogen atoms.

15. The compound of claim 2 wherein K has the formula:

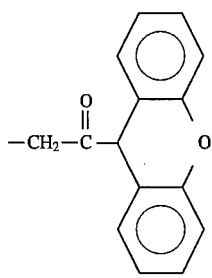

16. A composition for inhibiting the enzymatic activity of a serine protease or a cysteine protease comprising a compound of claim 1.

17. A method for inhibiting the enzymatic activity of a serine protease or cysteine protease comprising contacting a protease selected from the group consisting of serine protease and cysteine protease with an inhibitory amount of a compound of claim 1.

18. A method for inhibiting the enzymatic activity of a serine protease or cysteine protease comprising contacting a protease selected from the group consisting of serine protease and cysteine protease with an inhibiting amount of a compound of claim 2.

* * * * *

UNITED STATES PATENT AND TRADEMARK OFFICE
CERTIFICATE OF CORRECTION

PATENT NO. : 5,498,616
DATED : March 12, 1996
INVENTOR(S) : John P. Mallamo, Ron Bihovsky, Sankar Chatterjee & Rabindranath Tripathy It is certified that error appears in the above-identified patent and that said Letters Patent is hereby corrected as shown below:

Column 17, line 65, please delete "***$M^+$) Delete to M+)"

Column 23, line 6, please delete "690" and insert therefor --6.90--

Column 23, line 25, please delete "694" and insert therefor --6.94--

Column 23, line 39, please delete "(M+H)+" and insert therefor --$(M+H)^+$--

Column 23, line 40, please delete "$C_{31}H_{33}N5O_6$" and insert therefor --$C_{31}H_{33}N_5O_6$--

Signed and Sealed this

Twenty-third Day of July, 1996

Attest:

BRUCE LEHMAN

*Attesting Officer*   *Commissioner of Patents and Trademarks*